US006978779B2

(12) United States Patent
Haveri

(10) Patent No.: US 6,978,779 B2
(45) Date of Patent: Dec. 27, 2005

(54) VIBRATING ELEMENT LIQUID DISCHARGING APPARATUS HAVING GAS PRESSURE SENSING

(75) Inventor: Heikki Haveri, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 464 days.

(21) Appl. No.: 10/126,224

(22) Filed: Apr. 19, 2002

(65) Prior Publication Data

US 2003/0196660 A1 Oct. 23, 2003

(51) Int. Cl.[7] .......................... A61M 11/00; B05B 17/06

(52) U.S. Cl. ............................ 128/200.16; 128/200.14; 128/203.12; 128/204.22

(58) Field of Search ........................ 128/200.14, 200.16, 128/203.12, 203.15, 203.16, 204.21, 204.22, 205.23, 203.25; 600/459, 495, 532, 561

(56) References Cited

U.S. PATENT DOCUMENTS 3,812,854 A 5/1974 Michaels et al.
5,063,922 A * 11/1991 Hakkinen .............. 128/200.16
5,443,059 A 8/1995 Koch et al.
5,487,378 A 1/1996 Robertson et al.
5,865,171 A * 2/1999 Cinquin ................. 128/203.12
5,918,593 A * 7/1999 Loser .................... 128/200.16
5,964,219 A 10/1999 Pekka
6,085,740 A 7/2000 Ivri et al.
6,216,025 B1 * 4/2001 Kruger ........................ 600/407
6,539,937 B1 * 4/2003 Haveri .................. 128/200.21

FOREIGN PATENT DOCUMENTS

WO 01/76762 10/2001

* cited by examiner

*Primary Examiner*—Glenn K. Dawson
*Assistant Examiner*—Michael Mendoza
(74) *Attorney, Agent, or Firm*—Andrus, Sceales, Starke & Sawall, LLP

(57) ABSTRACT

A nebulizer determines the pressure and flow direction of the receiving gas for atomized liquid. A member of the apparatus is subjected to pressure exerted by the gas. The member is coupled to a bi-directional mechanical-electrical conversion element, such as a piezoelectric element, to form a pressure transducer. The member exerts a mechanical loading on the element responsive to the gas pressure to which it is subjected. In one embodiment, the element mechanically vibrates responsive to alternating electrical energization to discharge the liquid into the gas. The electrical admittance of the element is alterable by the mechanical loading applied to the element by the member. The difference between admittances measured in the loaded condition of the element and in an unloaded condition at the selected energization frequency is an indication of the pressure of the gas. By observing whether the magnitude of the admittance in the loaded state is greater or less than that in the unloaded state, the flow direction of the gas may also be determined. Or the flow direction may be determined by observing the changes in admittance as the frequency of the electrical energization is varied. In another embodiment, the piezoelectric element is not energized. The electrical output of the element, when subjected to a mechanical loading from the gas pressure, is used to detect gas pressures and/or as an indication of the gas pressure.

87 Claims, 21 Drawing Sheets

FIG. 13a
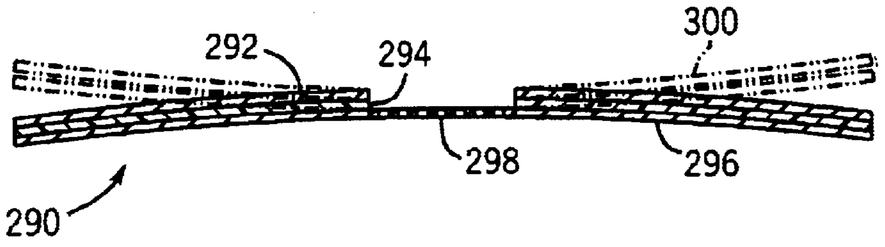
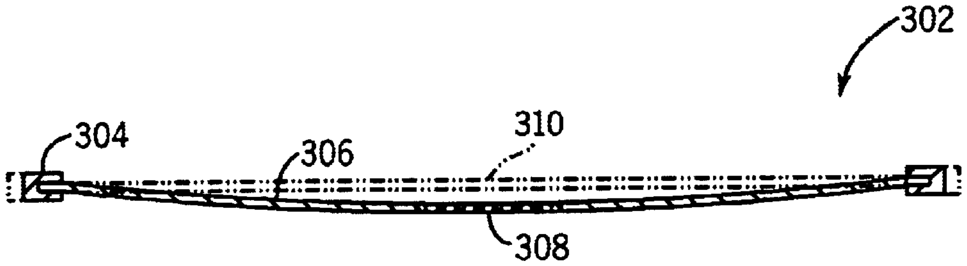
FIG. 13b
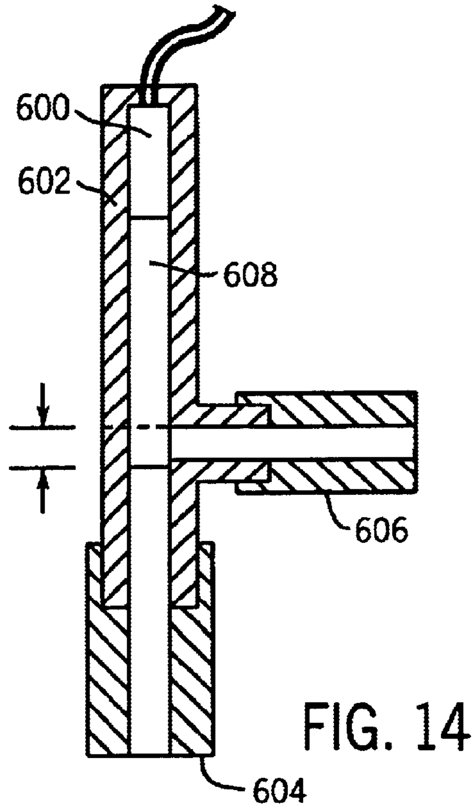
FIG. 14

VIBRATING ELEMENT LIQUID DISCHARGING APPARATUS HAVING GAS PRESSURE SENSING

BACKGROUND OF THE INVENTION

The present invention relates to an improved apparatus, such as a nebulizer apparatus, for discharging fluids, and to a method of operating same. Nebulizers, or atomizers, are devices that generate a fine spray or aerosol, usually of a liquid. A particularly useful application for nebulizers is to provide a fine spray containing a dissolved or suspended particulate or colloidal pharmaceutical agent for administration to a subject by inhalation. Such inhalation treatment is highly effective for conditions affecting the subject's respiratory organs. Further, since the lungs are close to the heart and the circulatory system of the body, drug administration by inhalation provides an effective and rapid delivery system for a drug to all organs of the body. In other applications, nebulizers provide a fine spray of water for humidification.

When used to dispense a pharmaceutical agent to a subject, a nebulizer in the form of an inhaler may be placed directly in the mouth or nose of the subject so that the spray can be entrained in the respiratory gases which are inhaled during normal, spontaneous breathing of the subject.

In other applications, the subject breathes with the aid of a respiratory ventilator. A typical ventilator has a breathing circuit comprising an inhalation limb and an exhalation limb connected to two arms of a Y-connector. The third arm of the Y-connector is connected, via a patient limb, to a mouthpiece, mask, or endotracheal tube for the subject. The ventilator provides a complete or partial supply of breathing gas to the subject through the inhalation limb during inhalation. The contraction of the subject's lungs discharges gases through the exhalation limb during exhalation. When a nebulizer is employed in conjunction with a ventilator, it is typically placed in the patient limb to discharge into the breathing gases inhaled by the subject but it can also be placed in the inhalation limb of the breathing circuit.

Nebulizers are currently in use that generate the spray either pneumatically or by means of ultrasonic vibrations. Pneumatic nebulizers are typically used with a liquid, such as an aqueous drug solution. High pressure driving gas is conducted through a nozzle to draw the drug from a drug supply to the nebulizer. The drug is discharged against a baffle or other similar separating means in a gas space of the nebulizer, breaking the liquid into a fine spray. The gas space is in fluid communication with the inhaled gas pathway for the subject so that the gas flow expelled from the nozzle along with the nebulized drug is conducted from the gas space to the pathway and ultimately to the subject.

Disadvantages in the use of pneumatic nebulizers include the following. If the nebulizer adds a significant quantity of gas, for example, up to five (5) liters/minute, into the breathing gases, the overall breathing gas composition to the subject may be significantly altered. Further, due to passage of the driving gas through the nozzle, the impingement of the drug on the baffle, etc., pneumatic nebulizers tend to be noisy. And, controlling the commencing and stopping of a drug spray is difficult and is not very accurate. This may result in wastage of the drug.

The foregoing shortcomings of pneumatic nebulizers have led to the use of ultrasonic nebulizers in which a fine spray is produced by ultrasonic vibration of the liquid containing the drug, as through the use of a piezoelectric crystal. The breathing gas composition and the on-off operation are easier to control with ultrasonic nebulizers than with a pneumatic nebulizer. However, ultrasonic devices require a large, bulky electrical power supply to power the crystal and may not be able to nebulizer colloidal or particulate suspensions.

In one type of ultrasonic nebulizer, the fine spray is produced by dropping the liquid on, or otherwise applying it to, the vibrating element. See Koeh et al. U.S. Pat. No. 5,443,059. Michaels et al., U.S. Pat. No. 3,812,854, describe another type of nebulizer for inhalation therapy in which the spray is generated on the front surface of a vibrating, porous body. The pores in the body form a network of passages that enable the liquid to flow through the body. The liquid to be nebulized is supplied under pressure from a liquid supply through a liquid conduit to the pores, and forced through the pores to the front surface of the porous body where it is discharged as a spray. Robertson et al., U.S. Pat. No. 5,487,378, describe a nebulizer in which the aerosol is formed using a mesh plate instead of a porous solid body. The mesh plate has a plurality of orifices through which the liquid can pass. Either the liquid or the mesh plate is vibrated ultrasonically by a piezoelectric element to nebulizer the liquid as it passes through the mesh plate.

A general shortcoming of current nebulizers is the efficiency with which the aerosol is transported into the subject's lungs. To increase the efficiency, the nebulizer may be operated so as to function in phase with the ventilator so that the aerosol is produced by the nebulizer either during, or partly during, inspiration by the subject. The proper timing can be achieved by switching the nebulizer on at the beginning of inspiration in response to a signal coming from the ventilator, or in response to information coming from a flow sensor as described in U.S. Pat. No. 5,964,219 to Pekka Merilainen.

However, a disadvantage currently exists in that to ensure that the nebulizer functions properly to achieve the best efficiency, a separate device is required to generate the necessary signal or information for optimal timing of the nebulization. This adds to the cost and complexity of the nebulizer and/or ventilator. For example, Ivri et al., U.S. Pat. No. 6,085,740, describe a nebulizer of the inhaler type in which the inhalation flow is detected from an audible signal produced during inhalation, which signal is then used to control the nebulization. In addition to cost and complexity, this approach may exhibit a sensitivity to external noise.

BRIEF SUMMARY OF THE INVENTION

An object of the present invention is to provide an improved apparatus and method for discharging fluids into a receiving gas flow and detecting changes in the pressure of the receiving gas. In a typical application, nebulized liquid is discharged into the breathing gas flow of a subject. The pressure detection so obtained may be used to sense the commencement of inspiration by the subject, or some other phase in the subject's respiratory cycle, to control operation of the nebulizer to provide nebulized liquid with a desired timing with respect to the subject's respiratory cycle. Typically, the commencement of inspiration would be determined and the supply of nebulized liquid would occur during, or partly during, the subject's inspiration as, for example, to administer a drug into the lungs of a subject.

The present invention thus avoids the need for the separate devices heretofore used in controlling the timing of the nebulization and introduction of the nebulized liquid into the receiving flow.

Another object of the present invention is to provide an improved apparatus and method for discharging fluid into a receiving gas flow and measuring the pressure of the receiving gas.

A further object of the present invention is to provide an improved apparatus and method for discharging fluid into a receiving gas flow and for determining the flow direction of the receiving gas.

In the present invention, the fluid discharging apparatus is placed in fluid communication with a receiving gas so that a member in the apparatus is subjected to pressure exerted by the receiving gas. When used to supply a drug, a liquid discharging apparatus in the form of a nebulizer may be placed in communication with the breathing gases pathway for a subject so that the member is subjected to the pressure of the breathing gases. The member of the apparatus that is subjected to pressure is coupled to a bi-directional mechanical-electrical conversion element, such as a piezoelectric element, to form a gas pressure transducer. The member exerts a mechanical loading on the element responsive to the gas pressure to which the member is subjected.

In an active embodiment of the invention, alternating electrical energization is applied to the element at a selected frequency. The element mechanically vibrates responsive to the application of the alternating electrical energization to the element to discharge the atomized liquid from the liquid discharging apparatus into the receiving gas. The energized element exhibits an electrical admittance. Admittance is the inverse of electrical impedance. The admittance of the element at the selected energization frequency is altered when the element is mechanically loaded by the member that is subjected to the pressure of the receiving gas.

The admittance exhibited by the element in an unloaded condition when energized by the electrical energy of the selected frequency is measured. When the member is subjected to the pressure of the receiving gas during operation of the fluid discharging apparatus to load the element, the admittance of the element is again measured. The difference between the admittances measured in the unloaded and loaded conditions is an indication of the pressure of the receiving gas.

The selected frequency used to energize the element may be the resonance frequency of the gas pressure transducer formed from the element and member or a frequency other than the resonance frequency.

By observing whether the magnitude of the admittance in the loaded state is greater or less than that in the unloaded state, a flow direction of the receiving gas may also be determined. Or, the flow direction may be determined by observing the changes in admittance as the frequency of the electrical energization is varied.

In another, passive, embodiment of the invention, no electrical energization is applied to the piezoelectric element of the pressure transducer. The voltage appearing at output terminals of the transducer is proportional to the mechanical loading applied to the element by the member which is subjected to the pressure of the receiving gas. The output voltage of the transducer is thus indicative of the receiving gas pressure.

As with the active embodiment of the invention described above, the transducer may have a plurality of mechanical resonance frequencies and a plurality of anti-resonance frequencies. The transducer may be constructed so that it is mechanically "tuned" to the frequency or dynamic properties of the receiving gas pressures to which it is subjected, thereby to maximize the voltage output of the transducer. This can be accomplished by appropriately establishing the dimensions and composition of the piezoelectric element and/or member subjected to the pressure of the receiving gas Various other features, objects, and advantages of the invention will be made apparent from the following detailed description and the accompanying drawings.

BRIEF DESCRIPTION OF THE SEVERAL VIEWS OF THE DRAWING

The present invention will be further understood by reference to the following detailed description and accompanying drawings, in which

FIGS. 13*a* and 13*b* are schematic views showing a further embodiment of a structure suitable for use in the present invention and incorporating a piezoelectric element;

FIG. 14 is a cross sectional view of another embodiment of a fluid discharging apparatus of the present invention.

DETAILED DESCRIPTION OF THE INVENTION

Figure 1:
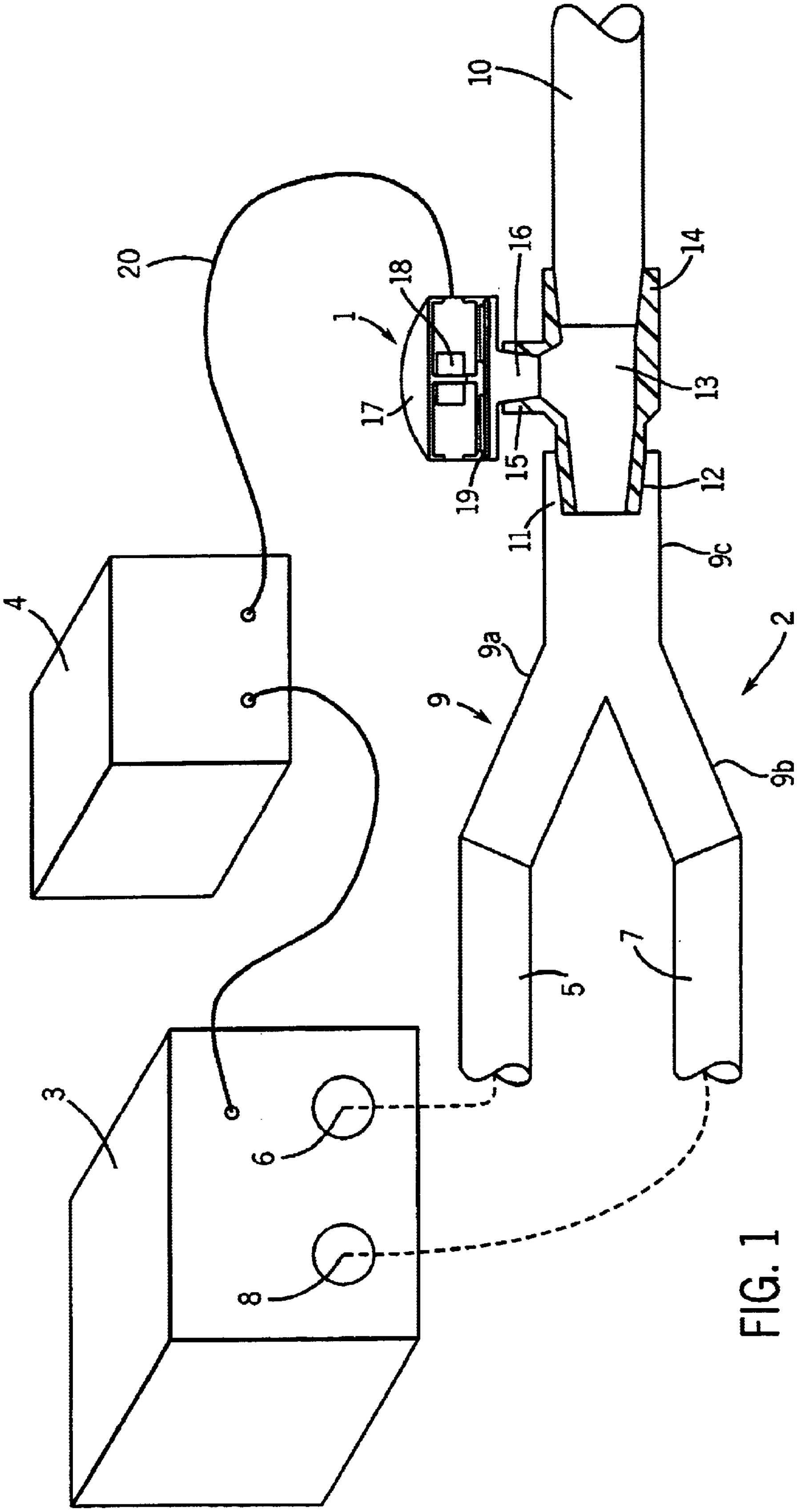
FIG. 1 is a somewhat schematic, cross-sectional view of a fluid discharging apparatus of the present invention in the form of a nebulizer connected to a breathing circuit which, in turn, is connected to a ventilator.

In the drawing figures, in which like reference numerals designate like parts throughout the disclosure, a fluid discharging and pressure sensing apparatus constructed according to the present invention is indicated generally by the reference numeral 1 in FIG. 1. In the application shown in FIG. 1, apparatus 1 is a nebulizer operatively connected to a breathing circuit 2 and a control unit 4. Control unit 4 is typically located separately from nebulizer 1 but may be incorporated in ventilator 3, if desired.

The substance to be nebulized typically comprises a solution, or a particulate or colloidal suspension, of a product but could comprise other substances, such as a dry fluid material. The substance may comprise water for humidification. For purposes of explanation, the fluid substance undergoing nebulization or atomization is hereinafter generally described as a liquid.

Nebulizer 1 atomizes the liquid for delivery in a breathing gas flow to a subject, for example, as a drug treatment for a patient. Breathing circuit 2 includes an inhalation limb 5, one end of which is coupled to ventilator 3 at inhalation limb connector 6, and an exhalation limb 7, one end of which is connected to ventilator 3 at exhalation limb connector 8. Inhalation limb 5 and exhalation limb 7 are connected at their opposite ends to two adjacent arms 9*a* and 9*b*, respectively, of a Y-connector 9. A third arm 9*c* of the Y-connector 9 is connected to one end of patient limb 10. The other end of patient limb 10 is directed to a gas administration structure (not shown) for the subject, such as a mouthpiece, a facemask, or an endotracheal tube.

When in use, ventilator 3 can selectively provide all or any predetermined portion of the breathing gases required by the subject by supplying breathing gases through the inhalation limb 5. The breathing gases pass from the ventilator 3, into inhalation limb 5, through Y-connector 9 and into patient limb 10 and are inhaled by the subject. On exhalation, the exhaled breathing gases pass from the subject through patient limb 10 and Y-connector 9, and into exhalation limb 7 back to the ventilator 3. The subject may also breathe spontaneously through patient limb 10.

As shown in FIG. 1, nebulizer 1 is preferably positioned in the breathing circuit 2 as near as possible to the subject to minimize the length of the aerosol transport path from the nebulizer 1 to the subject, and to minimize the deposition of the atomized liquid on the interior walls of the breathing circuit 2. To this end, nebulizer 1 is preferably attached in the breathing circuit 2 between the Y-connector 9 and the patient limb 10. The third arm 9*c* of the Y-connector 9 has a socket 11 sized for patient limb 10 which can alternatively receive a tubular projection 12 of an adapter 13 for mounting nebulizer 1. The adapter 13 includes a first tubular socket 14, disposed opposite the Y-connector 9, and formed similarly to the socket 11, that receives the patient limb 10. The adapter 13 also has a second tubular socket 15 in which nebulizer 1 is positioned. To secure nebulizer 1 to the adapter 13, the nebulizer includes a downwardly extending tubular projection 16 that is insertable into the second socket 15. When nebulizer 1 is not needed, or when the nebulizer is removed for cleaning or maintenance, a removable cap (not shown) may be fitted into or over the second socket 15 to allow breathing circuit 2 to function in a normal manner. Alternatively, the entire adapter 13 may be removed from the breathing circuit 2 so that the patient limb 10 can be connected directly to the Y-connector 9.

Nebulizer 1 also includes a liquid reservoir 17 for holding the liquid to be nebulized. In the embodiment shown in FIG. 1, reservoir 17 is removably mounted on the top of the nebulizer 1 opposite the projection 16. Alternatively, it may be separate from the nebulizer 1 and connected to the nebulizer 1 by a suitable conduit.

Figure 2:
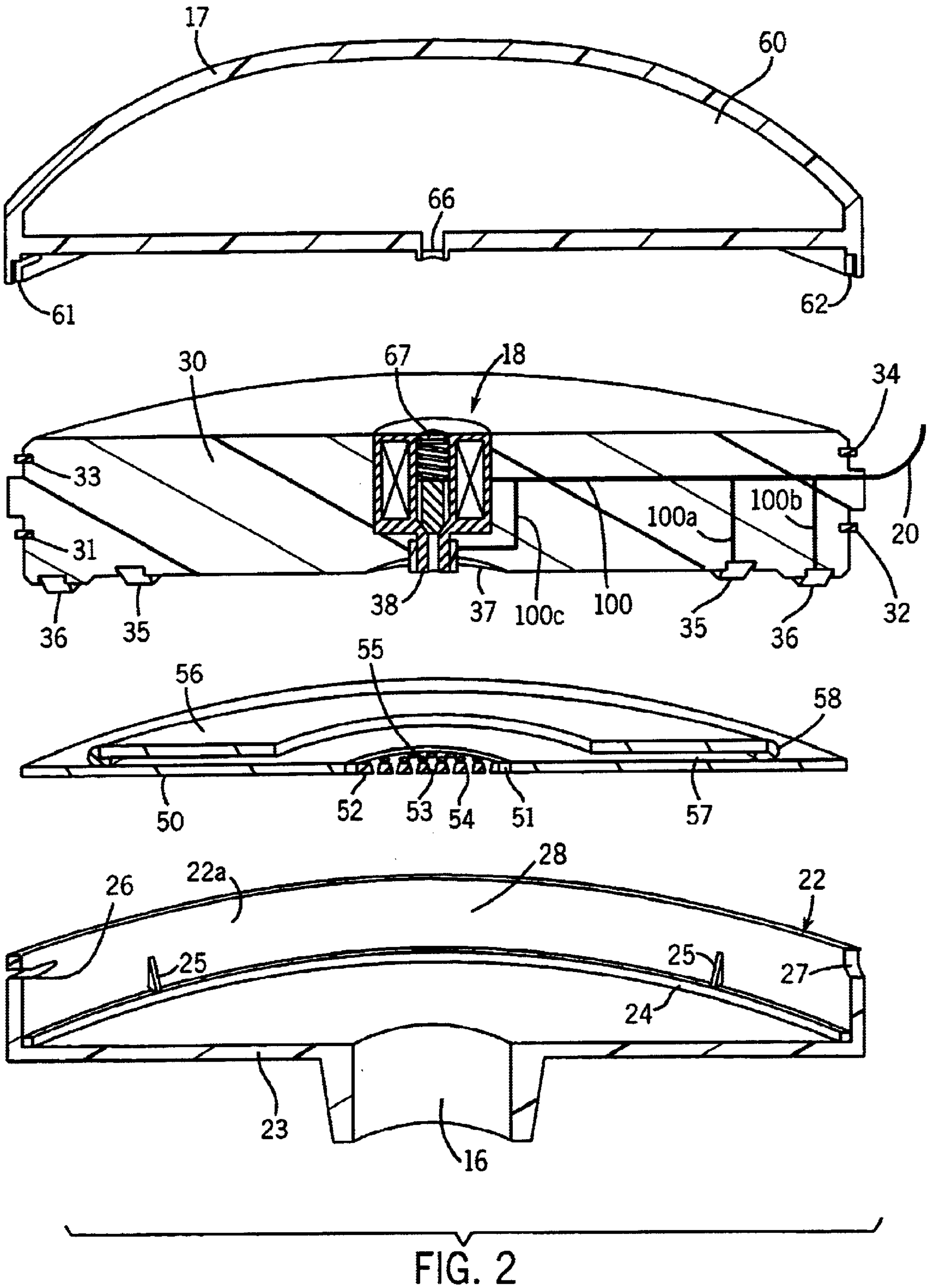
FIG. 2 is an exploded, cross-sectional view of the apparatus of FIG. 1.

Referring now to the detailed, exploded view of FIG. 2, the lower portion of the nebulizer 1 is formed by an annular housing 22 that includes the tubular projection 16 which extends downwardly from the housing 22. Housing 22 may be formed of a generally rigid material such as a hard plastic or similar material and defines a cavity 28 therein. An O-ring 24, made of a resilient material, such as rubber, is positioned around the periphery of a planar base member 23 which forms the bottom of the housing 22. The housing 22 also includes a number of inwardly extending protrusions 25 disposed on a circular sidewall 22*a* of the housing that serve to engage and retain the O-ring 24 within the housing 22.

Housing 22 receives and retains an internal plug member 30 within the cavity 28. Plug member 30 is releasably retained within the cavity by a spiral or bayonet fastening means formed, in part, by openings 26 and 27 located on the side wall 22*a* of the housing 22. Associated projections 31 and 32 are situated symmetrically on opposite sides of plug member 30 and fit into the openings 26 and 27 formed in the housing 22. Plug member 30 may be separated from, or joined to, housing 22 by turning and pulling or pushing and turning the plug member 30 with respect to housing 22. This allows the plug member 30 to be removed at the end of therapy, for replacement or for cleaning when a different pharmaceutical agent is to be subsequently administered to the subject.

Disc-like plate 50 is disposed between the base member 23 and the plug member 30. The plate 50 may be positioned inside the cavity 28 of housing 22 between the upper surface of O-ring 24 and the lower ends of protrusions 25. Plate 50 is spaced from base member 23 in order to prevent the base member and the adjacent face of the plate 50 from touching. Plate 50 is made of a conductive material, such as a conductive metal, and contains central opening 51. Preferably, the plate 50 is made of brass. A mesh plate 52 is attached to plate 50 within the central opening 51. Mesh plate 52 may be mounted to the plate 50 by any suitable technique, including, for example, brazing or welding. Plate 50 and mesh plate 52 may also be unitarily formed from a single sheet of material, if desired.

The mesh plate 52 is a relatively thin plate having a plurality of holes or pores 53 extending through the mesh plate 52 to discharge liquid, as hereinafter described. Mesh plate 52 may be between about 0.01 and 0.04 mm thick, and preferably is about 0.02 mm thick. The diameter of the holes 53 at the lower surface 54 of the mesh plate 52 is about 1 to 25 $\mu$m, and is preferably approximately 2–10 $\mu$m. The holes 53 may be formed in the mesh plate 52 by an electroforming process, which produces the holes 53 such that they have a diameter that decreases in a direction from the rear surface 55 to the front surface 54 of mesh plate 52. However, holes 53 will function equally well if their diameter is uniform along their length as the primary criterion for the holes 53 is that the exit diameter in lower surface 54 of mesh plate 52 be sufficient to form liquid droplets of a desired size.

A ring-like vibrating element 56, is mounted to the upper surface of plate 50. An element formed of piezoelectric material may be used as vibrating element 56. A piezoelectric material possesses the property of changing its dimensions when subjected to an electrical energization. The reverse is also true. That is, when the dimensions of a piezoelectric material are changed, as by compressing or stretching it, electrical energy is generated in the material. Thus, a piezoelectric element can convert electrical energy into mechanical energy, and vice versa. As hereinafter noted, a unique feature of the present invention is to employ both these conversion characteristics in the operation of the liquid discharge apparatus.

Figure 3A:
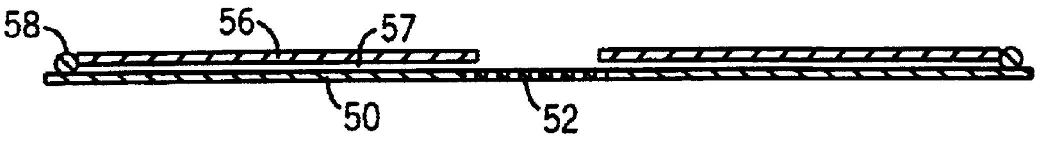
FIGS. 3*a*, 3*b* and 3*c* are schematic views showing the operation of vibrating and atomizing components of the apparatus of FIG. 1.

The piezoelectric element 56 is positioned above the plate 50 by a small distance to define a gap 57, shown most clearly in FIG. 3*a*, between the element 56 and the plate 50. The piezoelectric element 56 is secured above the plate 50 by a positioning means 58 which can retain the element 56 in a position spaced the small distance above the plate 50. This positioning means 58 can be a brazed connection, a weld, a conductive glue or other suitable composition capable of holding the element 56 above the plate 50. Piezoelectric element 56 includes a central opening. Plate 50 and piezoelectric element 56 form a pressure transducer, as hereinafter described in detail.

The plug member 30 is formed from a non-conductive, generally rigid material, such as a hard plastic, and includes a first terminal 35 and a second terminal 36 made of conductive material that are disposed on the bottom of the plug member 30. Both terminals 35 and 36 are preferably in the form of ring-shaped conductors that are resilient or resiliently mounted in plug member 30 and that extend concentrically around the bottom of the plug member 30. However, each terminal 35 and 36 can have any form capable of electrically engaging the piezoelectric element 56 and plate 50, respectively. The first terminal 35 and second terminal 36 are connected to cable 100 within the plug member 30 by a pair of branch connectors 100*a* and 100*b*, respectively. Cable 100 is connected to cable 20 which is connected to control 4. Via the branch connectors 100*a* and 100*b*, power can be supplied to, and signals can be received from, the terminals 35 and 36, respectively. When the plug member 30 is placed on top of plate 50 so that the plate 50 is positioned between the plug member 30 and the O-ring 24, the first terminal 35, contacts piezoelectric element 56 and second terminal 36 contacts conductive plate 50. Terminal 36 may be electrically grounded for purposes of applying a desired voltage to piezoelectric element 56 in conjunction with terminal 35.

The plug member 30 also encloses liquid flow controlling valve 18 which is disposed concentrically within the plug member 30. Valve 18 is connected to the control unit 4 by cable 100, 20 and is used for controlling the supply of the liquid to vibrating mesh plate 52 from the liquid reservoir 17. Valve 18 may comprise a spring loaded ferromagnetic valve member that closes a valve seat. Valve member is lifted off the valve seat when a surrounding magnetic coil is energized through cable 100, 20 to supply liquid from reservoir 17 to mesh plate 52.

Reservoir 17 comprises a liquid chamber 60 attached to the top surface of plug member 30 by spiral or bayonet fastening openings 61 and 62 located on opposite sides of the chamber 60. A pair of projections 33 and 34 are situated symmetrically on opposite sides of plug member 30 and fit into the openings 61 and 62 formed in the chamber 60. The chamber 60 may be fastened to, or unfastened from, plug member 30 by pushing and turning or turning and pulling the chamber 60 with respect to plug member 30. This allows the chamber 60 to be removed at the end of therapy for replacement, or for the subsequent administration of a different drug to the subject.

The chamber 60 includes an outlet opening 66 through which the liquid to be nebulized passes from the chamber 60. When chamber 60 is connected to the plug member 30, the outlet opening 66 engages a depression 67 in the valve 18 so that, when the valve 18 is opened, liquid can flow from the chamber 60, through the outlet opening 66 and through valve 18. Opening 66 may also be used to fill chamber 60 with liquid, if desired. Chamber 60 is typically pressurized, as be a flexible membrane or external pressure source, to assist in the discharge of liquid from the reservoir.

Plug member 30 further includes a tubular sensing electrode 38 that is located adjacent the upper surface 55 of mesh plate 52 when the plug member 30 is placed in the housing 22 over the plate 50. As shown in FIG. 2, tubular sensing electrode 38 may surround the outlet from valve 18. The electrode 38, in conjunction with mesh plate 52 which is spaced below sensing electrode 38, is used to measure the impedance created by the presence of a column of liquid between the outlet of valve 18 and mesh plate 52. Branch connector 100*c* connects electrode 38 to cables 100, 20 and to the control unit 4 in the course of performing an impedance measurement. A small domed cavity 37 is disposed in the lower surface of plug member 30 and surrounds the sensing electrode 38 to facilitate impedance measurement.

To operate nebulizer 1, valve 18, which is used for supplying liquid to vibrating mesh plate 52, is initially opened in response to a signal from the control unit 4 sent through the cable 20, 100. Liquid flows from the opening 66 of chamber 60 through the open valve 18 toward the mesh plate 52. With continued supply of liquid, the cohesive forces in, and surface tension of, the liquid create a column of liquid that extends between the lower end of the valve and sensing electrode 38 and the mesh plate 52. The sensing electrode 38 and mesh plate 52 detect the presence and magnitude of the amount of liquid between the sensing electrode 38 and the rear surface 55 of mesh plate 52 by an alteration of the impedance between the two elements due to the presence or absence of liquid between the electrode 38 and the mesh plate 52.

A signal from mesh plate 52 is obtained via terminal 36 and a signal from sensing electrode 38 is obtained via cable branch 100*c*. The signals from the mesh plate 52 and the electrode 38 are transmitted through the cable 20 to an impedance sensor (not shown) disposed in the control unit 4. When the signal indicates a liquid volume in the column that equals or exceeds a desired value, the control unit 4 operates valve 18 to close the valve and terminate the supply of liquid to the column. As liquid is discharged by nebulizer 1, the size of the column of liquid is reduced. When the impedance signal obtained by the electrode 38 and mesh plate 52 indicates that the volume of liquid is below the desired value, due to the discharge of liquid through the mesh plate 52 during operation of nebulizer 1, the control unit 4 reopens the valve 18 to allow more liquid to be supplied through the valve.

Figure 3B:
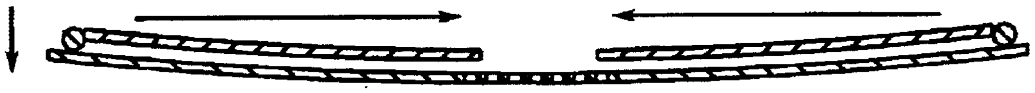
Figure 3C:
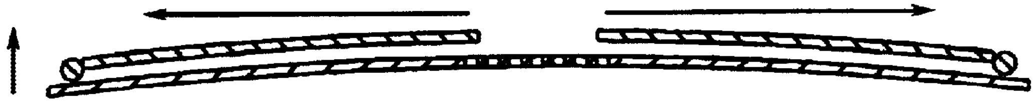

FIG. 3*a* is a simplified showing of piezoelectric element 56 and plate 50 in a state in which no voltage or energization is applied to the former. When high frequency alternating electrical energization is supplied to piezoelectric element 56 from a power source (not shown) inside control unit 4 through cable 20, 100 and terminals 35 and 36 the element will vibrate. The electrical energization causes the piezoelectric element 56 to alternately contract from the unenergized equilibrium state, shown in FIG. 3*a*, to a radially decreased state shown in FIG. 3*b* and then expand to a radially increased state shown in FIG. 3*c*. Due to the fact that the piezoelectric element 56 is joined to plate 50 about the periphery of the element 56, the radial reduction of piezoelectric element 56 causes plate 50 to bow in a downward direction as shown in FIG. 3*b*. Radial expansion of piezoelectric element 56 causes the element and plate 50 to bow upwardly as shown in FIG. 3*c* as a result of unsymmetrical forces occurring in these components from their peripheral joinder. When the plate 50 and element 56 alternatingly shift from the radially decreased condition shown in 3*b* to the radially increased condition shown in FIG. 3*c* and vice versa, the plate 50 moves through a flat or normal condition corresponding to that shown in FIG. 3*a*.

Due to the motion of plate 50 shown in FIGS. 3*a*, 3*b* and 3*c*, nebulized liquid is discharged from holes 53 in mesh plate 52. At the front surface 54 of the vibrating mesh plate 52, the discharged liquid will grow into drops at the front end of each hole 53 due to the surface tension of the liquid. The drops will increase in size until the expelling forces arising from the oscillating movement of mesh plate 52 and the mass of each drop exceeds the holding force determined by the size of the holes 53 in mesh plate 52 and the surface tension of the liquid. The drops expelled from plate 52 then pass through tubular projection 16 of housing 22 into the patient limb 10 of the breathing circuit 2 and are inhaled with the breathing gases by the subject as a nebulized or atomized liquid.

In the operation described immediately above, piezoelectric element 56 converts electrical energy into mechanical energy to cause the plate 50 to oscillate and discharge liquid from holes 53 in mesh plate 52 as a result of the mechanical deflection shown in FIGS. 3*a–c*. However, as noted above, a piezoelectric element can also convert mechanical energy to electrical energy. This characteristic is used in the present invention to obtain information about the breathing gases in the breathing circuit 2, and particularly the pressure of such gases. When the housing 22 is secured to the adapter 13, lower surface of plate 50 and the front surface 54 of mesh plate 52 are exposed to the pressure of the breathing gases flowing through the breathing circuit 2. This pressure will vary significantly during inhalation and exhalation conditions in breathing circuit 2. For example, when the ventilator 3 is producing entirely artificial ventilation for the subject, breathing gas pressures in the breathing circuit 2 may increase up to one hundred (100) mbar during inspiration and thereafter decrease during expiration. When the patient breathes spontaneously, the effect will be just the opposite, i.e., breathing circuit pressure will decrease during inspiration and increase during expiration.

The O-ring 24 separating the plate 50 from the base member 23 effectively seals the space between the plate 50 and base member 23 of housing 22. As a result, the effects of the changing breathing gas pressures in breathing circuit 2 are present within the space between the plate 50 and the base member 23. This is volume 65 shown in FIGS. 4 and 5.

Figure 4A:
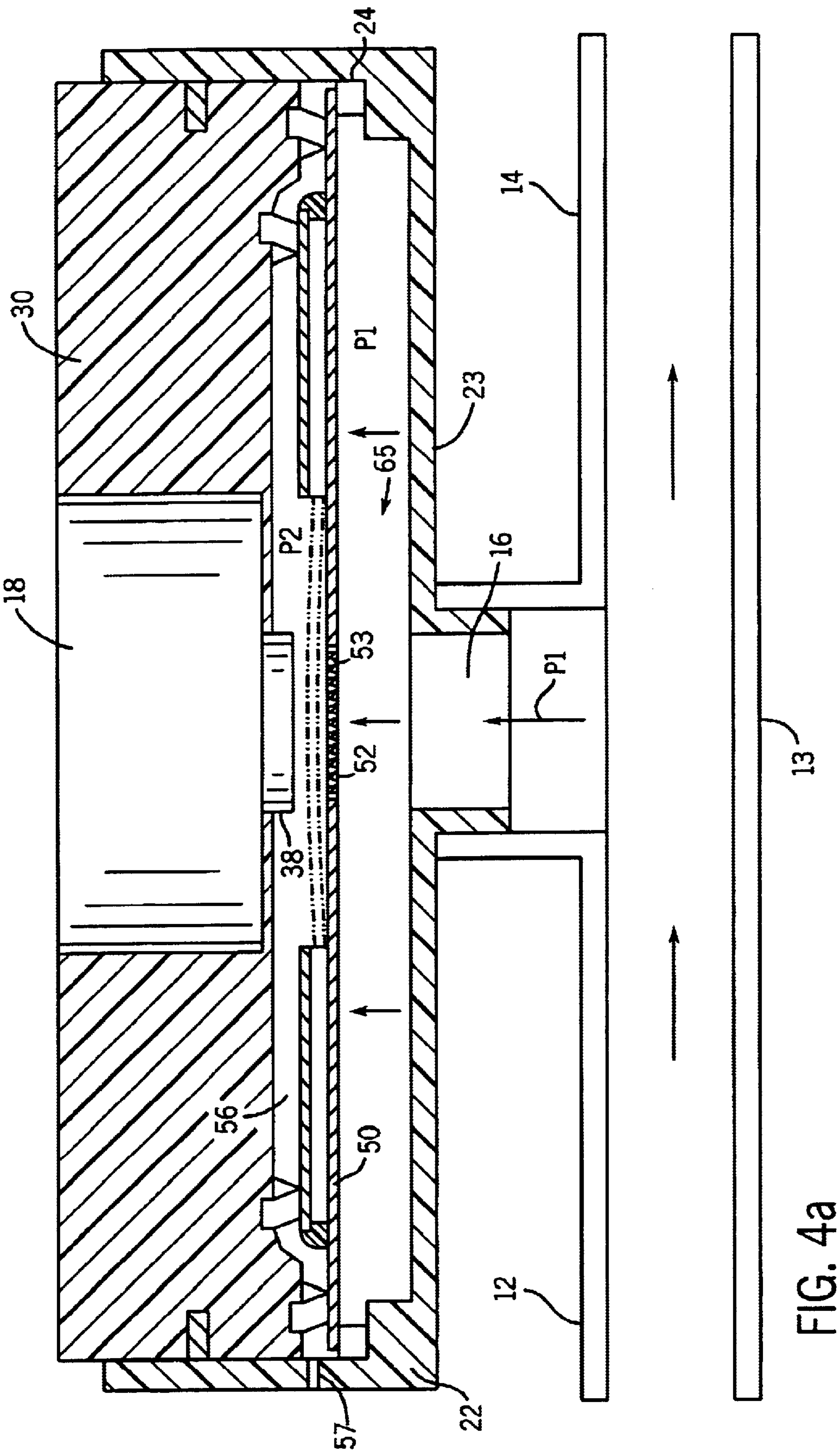
FIGS. 4*a* and 4*b* are schematic cross-sectional views of the apparatus of FIG. 1 showing operation under conditions in which a subject is breathing with the aid of a ventilator.

FIG. 4*a* shows conditions in nebulizer 1 when breathing gases are being provided to a subject by ventilator 3. The gas pressure in breathing circuit 2 is increased by ventilator 3 during inspiration. The pressure in volume 65, formed between plate 50 and base member 23 and sealed by O-ring 24 is similarly increased, due to the communication of the volume 65 with the breathing circuit 2 through the opening of tubular projection 16. When liquid is fed to the mesh plate 52 from valve 18, the liquid column extending between the lower end of valve 18 and mesh plate 52 blocks the holes 53 in mesh plate 52. This prevents the gas pressure created in the volume 65 from passing through the holes 53 of mesh plate 52. Therefore, the increasing pressure in the volume 65, illustrated as the upward arrow P1 in FIG. 4*a*, acts to bend plate 50 upwardly and away from adapter 13, as shown by the dotted line in FIG. 4*a*. The pressure on the upper side of plate 50, illustrated as pressure P2 in FIG. 4*a*, remains constant at the atmospheric pressure provided through bleed passage 57 in housing 22. The atmospheric pressure is lower than the increased pressure P1 provided by ventilator 3. When the breathing gas pressure in breathing circuit 2 decreases during expiration, the plate 50 is restored to the state shown in FIG. 4*b*.

Figure 4B:
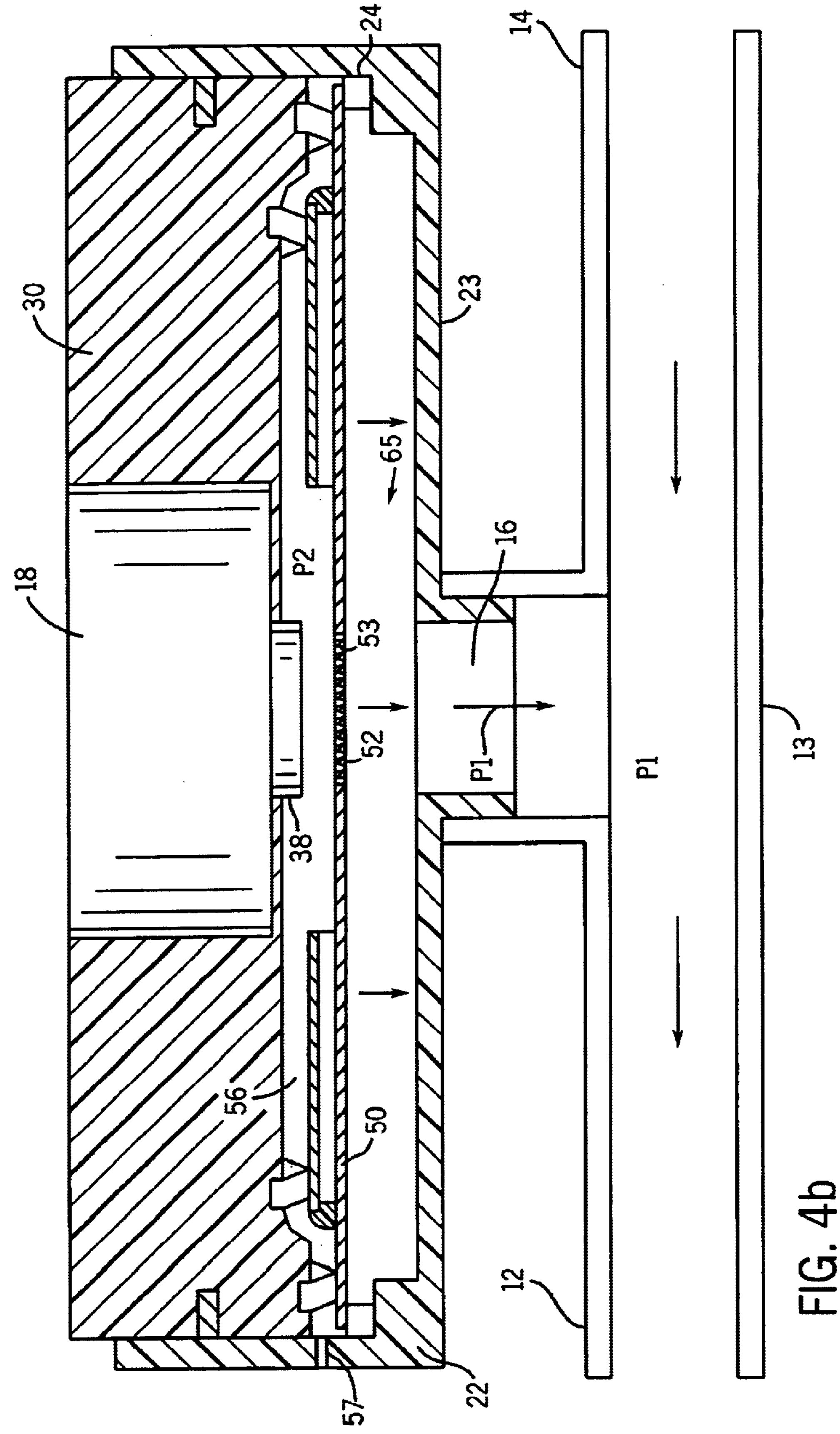
Figure 5A:
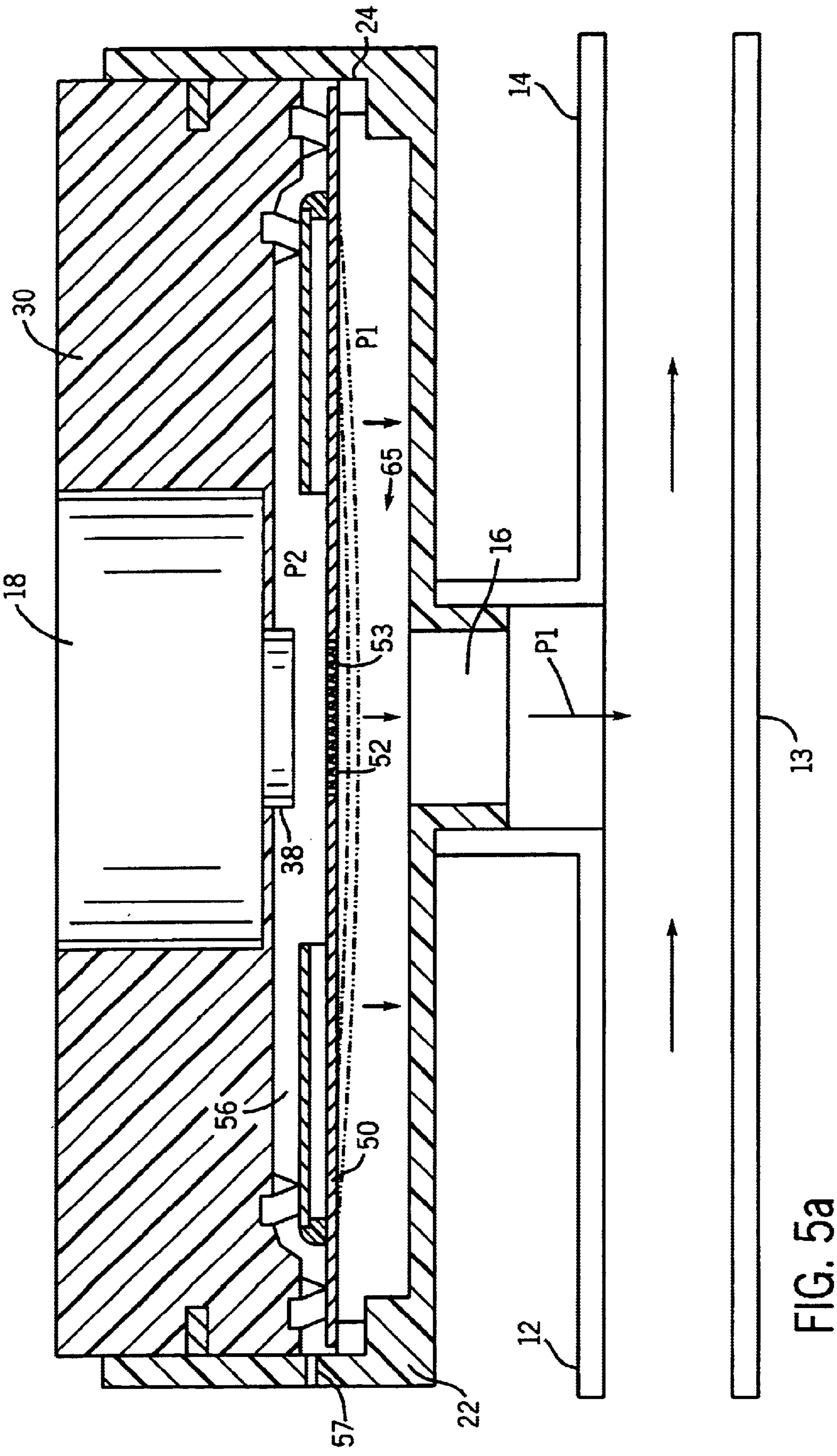
FIGS. 5*a* and 5*b* are schematic cross-sectional views of the apparatus of FIG. 1 similar to FIGS. 4 and 4*a* but showing operation under conditions in which a subject is breathing spontaneously.
Figure 5B:
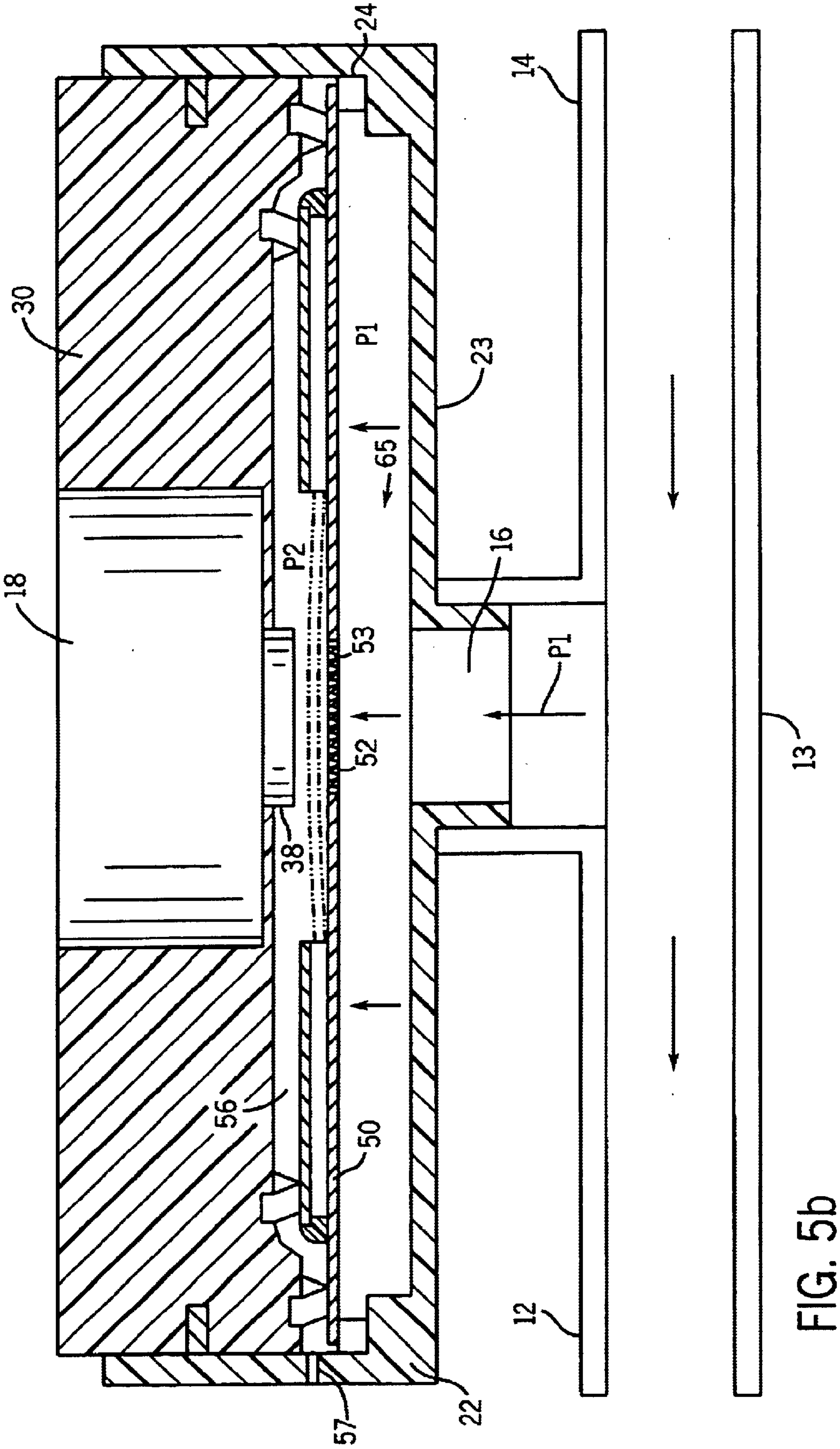

FIGS. 5*a* and 5*b* are similar to FIGS. 4*a* and 4*b* and show circumstances occurring when the subject is breathing spontaneously. The breathing gas pressure inside adapter 13 and volume 65 decreases during inspiration by the subject as the diaphragm of the patient falls to draw breathing gases into the lungs. This reduction in pressure in volume 65, shown as the downward arrow P1 in FIG. 5*a*, causes the plate 50 to bend towards the adapter 13. When the breathing gas pressure increases during expiration by the subject, as shown by the upwardly extending arrow P1 in FIG. 5*b*, plate 50 bends upwardly in a direction away from adapter 13, also as shown in FIG. 5*b*.

The deflections of the piezoelectric element 56 shown in FIG. 3 result in a change in the dipole moment of the piezoelectric material forming the element 56. This causes a voltage to be generated in the element 56 and a signal to appear at terminals 35 and 36 of nebulizer 1.

The bi-directional electromechanical conversion properties of piezoelectric element 56 enable the element 56 to be used in two ways. First, they can be used to create mechanical vibrations in a piezoelectric element 56 and plate 50 for atomization of liquid. This is electrical to mechanical conversion. Second, they can be used to electrically measure the mechanical strains in element 56 caused by the external forces applied to the piezoelectric element 56 resulting from breathing gas pressures in breathing circuit 2 acting on plate 50 in the manner described in FIGS. 4 and 5. This is mechanical to electrical conversion. The effects of these conversions are most pronounced when they occur along the poling axis of the piezoelectric element established during manufacture and piezoelectric element is formed and mounted to plate 50 such that this will occur. The poling axis will be generally parallel to the plane of ring-like piezoelectric element 56.

When a mechanical force or electrical energization is applied to a piezoelectric element that does not thereafter change or changes only very slowly, the conversion occurring in the piezoelectric element is somewhat ineffective. For example, the dimensional change in a piezoelectric element resulting from the application of a DC electrical energization is usually measured in nanometers. The conversion from mechanical energy to electrical energy is somewhat more effective and becomes more effective if the mechanical force is rapidly applied. For example, delivering a sharp blow to a piezoelectric element results in an output voltage spike.

When electrical energization that alternates in polarity is applied to a piezoelectric element, the piezoelectric element undergoes mechanical vibration at a frequency corresponding to that of the alternating electrical energization. A piezoelectric element, like other mechanical objects and structures, will have a natural frequency of vibration. When vibrating at the natural frequency, physical displacements in an object are at a maximum amplitude. When the frequency of the alternating electrical energization is that of the natural frequency of the piezoelectrical element, the condition is one of mechanical resonance. When converting electrical energy into mechanical energy at the frequency of mechanical resonance of the piezoelectric element, the maximum amplitude of mechanical displacement induced in the piezoelectric element by the alternating electrical energization is much greater, for example, 10–100 times greater, than the maximum displacement that can be obtained from the application of electrical energization that does not change or changes very slowly after application.

To consider the conversion of mechanical energy to electrical energy when a piezoelectric element is driven at the frequency of mechanical resonance, the electrical characteristics of the piezoelectric element may be illustrated by the simple equivalent circuit 68 shown in FIG. *6a*. In the equivalent circuit, capacitance 70 is the capacitance of the piezoelectric element and resistance 72 is the dielectric loss of the piezoelectric element. Resistor 74 represents the mechanical loss in the piezoelectric element and resistance 76 represents the mechanical load on the transducer, such as that imposed by plate 50. Capacitor 78 and inductor 80 represent the rigidity and mass of the material of the piezoelectric element, respectively.

The series and parallel connections of the capacitive and inductive components in the equivalent circuit shown in FIG. *6a* cause the overall circuit impedance characteristics to vary with frequency. When a piezoelectric element is vibrated at the frequency of mechanical resonance, the impedance of the piezoelectric element is at its lowest value. The inverse expression of impedance is "admittance," which quantity is used herein for ease of explanation. The admittance of piezoelectric element will be at its greatest value at the frequency of mechanical resonance of the piezoelectric element. Conditions at this frequency resemble the characteristic of a series connected, inductive-capacitance alternating current circuit and are sometimes called that of electrical "resonance."

In addition to the high admittance characteristics appearing at the frequency of mechanical resonance, there will also be a vibration frequency at which the admittance of the piezoelectric element will be at a minimum value. Conditions at this frequency resemble those of a parallel inductive-capacitance alternating current circuit and this point is sometimes called that of electrical "anti-resonance."

In FIG. *6b*, the ordinate is scaled in the electrical admittance Y of the piezoelectric element. The abscissa is scaled in the frequency. The graph 200 of FIG. *6b* shows the electrical admittance Y of a piezoelectric element with respect to the mechanical frequency of the element. The frequency, 202 at which the admittance Y is at a maximum value, is the mechanical resonance frequency of the piezoelectric element. The minimum value of admittance Y is found at frequency 204 which is characterized as the anti-resonance frequency.

The frequency of mechanical resonance of a piezoelectric element is established by the external dimensions of the element and/or the composition of the piezoelectric material forming the element and can be changed by changing these aspects of the element.

When the piezoelectric element is attached to another mechanical element, for example, plate 50 as shown in FIG. 3 to form a pressure transducer, the attachment affects the mechanical resonance frequency of the piezoelectric element. The attached element functions as the mechanical load to the piezoelectric element. The attached mechanical element will not necessarily vibrate at the same frequencies as the piezoelectric element so that the overall composite transducer construction may have a plurality of mechanically resonant frequencies at which the admittance Y is at high values and a plurality of anti-resonant frequencies at which the admittance has low values.

FIG. *6c* shows, in a manner similar to FIG. *6b*, a graph 206 of admittance Y versus frequency for a composite structure, such as that described above. Vibration of the composite structure at frequencies 208, 210, and 212 produce high values of admittance. Vibration at frequencies 214 and 216 produce low values for admittance Y.

As generally indicated in FIGS. *6b* and *6c*, the admittance Y values at the peaks of the resonance frequencies are from several to 100 times higher than those values found in the lower portions of the graph. The width of the peaking portions of the admittance frequency graphs, in terms of frequency at −3 dB admittance level, is usually from tens of hertz to several kilohertz, depending on the structure of the piezoelectric element and/or composite structure.

Figure 6A:
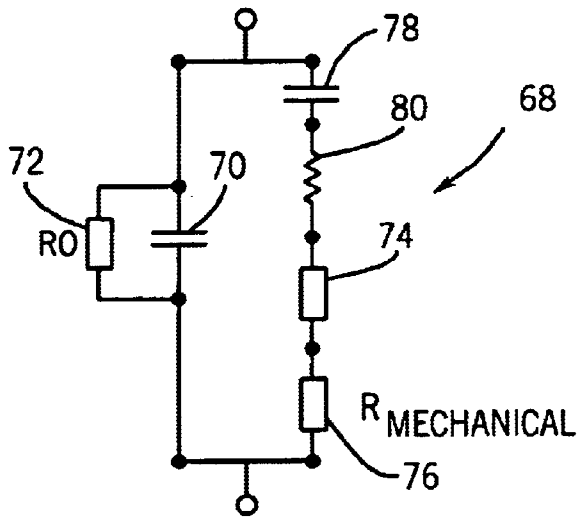
FIG. 6*a* is an equivalent electrical circuit diagram of a structure incorporating a piezoelectric element which may be used as a transducer in the apparatus of FIG. 1.
Figure 6B:
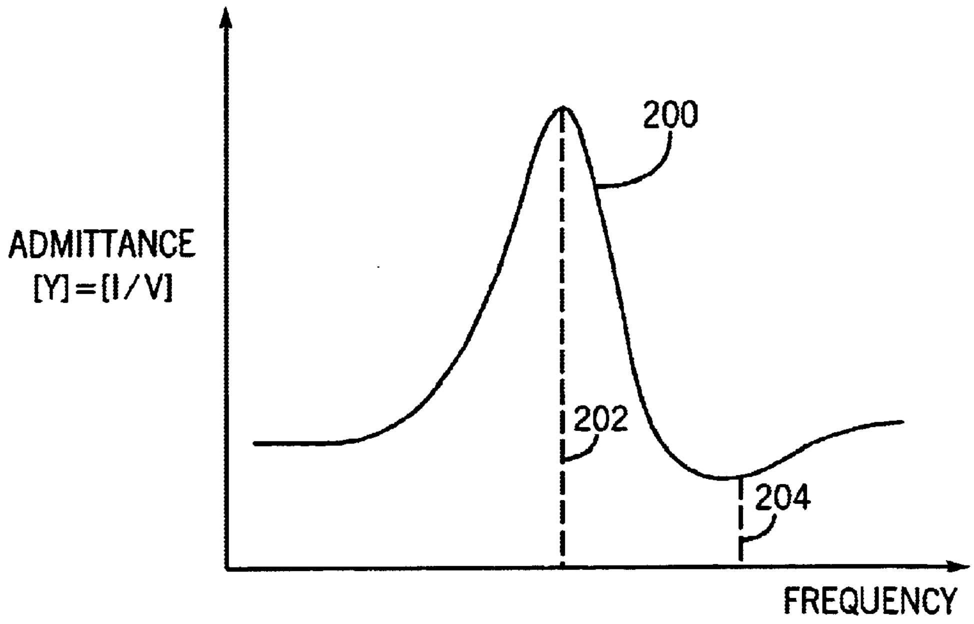
FIG. 6*b* graphically illustrates a resonance curve of a piezoelectric element.
Figure 6C:
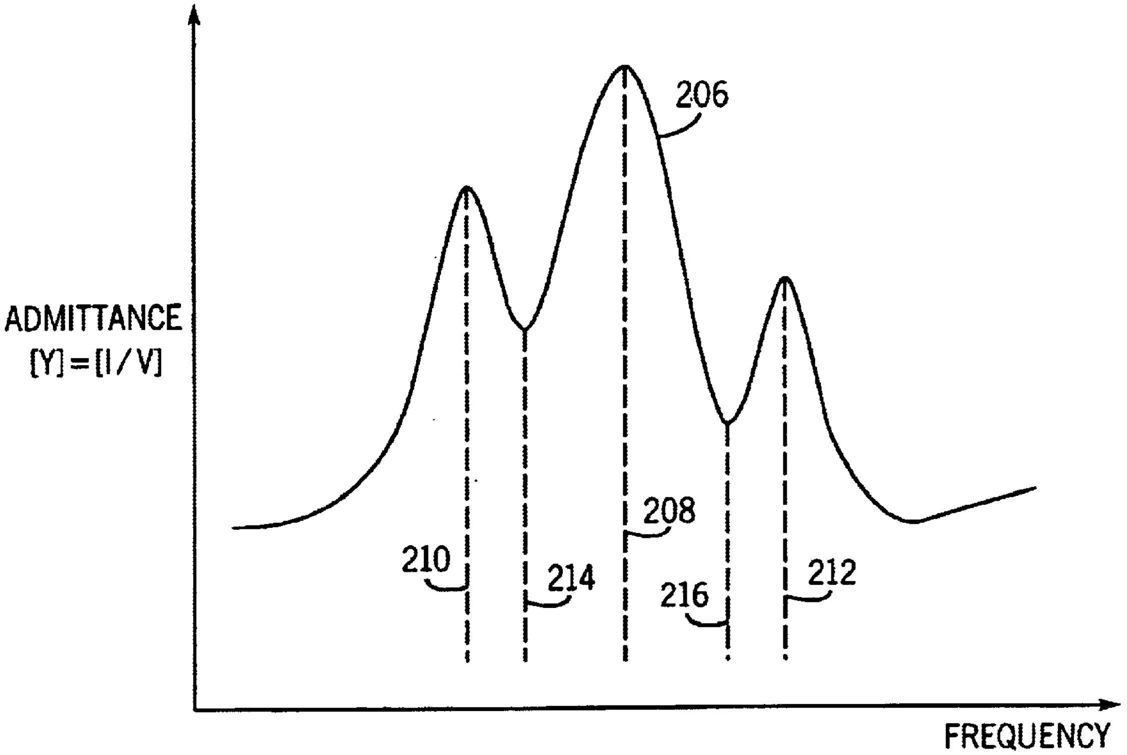
FIG. 6*c* graphically illustrates a resonance curve for a structure incorporating a piezoelectric element.

The graphs shown in FIG. 6 may be obtained by measuring the current through a piezoelectric element against the frequency of the electrical signal applied to the piezoelectric element when an alternating electrical energization of constant peak voltage magnitude is applied to the piezoelectric element. The measured current is used to compute the admittance of the piezoelectric element. The frequency that produces the highest current, and hence highest admittance, is the mechanical resonance frequency of the element. FIG. *7a* shows a circuit that may be used to determine the admittance of a composite construction containing a piezoelectric element. Piezoelectric element 56 is connected in series with ammeter 220 across constant peak voltage magnitude, variable frequency AC voltage source 222. As the frequency of voltage source 222 is varied, the current through piezoelectric element 56 is measured and the admittance determined as Y=I/V.

Or a current that alternates between fixed magnitudes may be applied to the piezoelectric element as shown in FIG. *7b*. The current source 224 is of adjustable frequency. The voltage across the piezoelectric element is measured by voltmeter 226 as the frequency of the applied current is varied. With the current magnitude so fixed, the voltage across the piezoelectric element will decrease as the admittance of the piezoelectric element increases at the frequency of mechanical resonance. The same formula, Y=I/V, is used to determine admittance.

A third way to establish the data shown in FIG. 6 is to measure electrical phase differences occurring in the circuit containing piezoelectric element 56. At the frequency of mechanical resonance, there will be a minimum phase difference, or no phase difference, between the voltage and current in the circuit. See FIG. *7c* in which the phase difference may be determined by voltage and load current measurements carried out in connection with resistor 228 and voltage source 230.

In the operation of nebulizer 1, piezoelectric element 56 is preferably electrically energized at the frequency 208 shown in FIG. *6c* to vibrate the composite pressure transducer structure with maximum magnitude mechanical deflections occurring in plate 50, thereby to provide highly desirable atomization to the liquid being nebulized. However, the piezoelectric element may also be energized at frequencies 210 or 212 to vibrate plate 50 and produce atomization if the maximum resonant frequency 208 is out of a desired operating frequency range.

An external compressive or tensile load applied to the vibrating piezoelectric structure as when plate 50 is subjected to the breathing gas pressures in breathing circuit 2 shifts the series resonance frequency or frequencies, such as 202, 208, 210 and 212 and the parallel or anti-resonant frequency or frequencies, such as 204, 214, and 216. The shift in resonance and anti-resonance frequencies will be related to the magnitude of the applied load. Furthermore, the shift in resonance and anti-resonance frequencies for a given applied load is greater when the effect of external force is directed along the poling axis of the piezoelectric element.

Figure 8A:
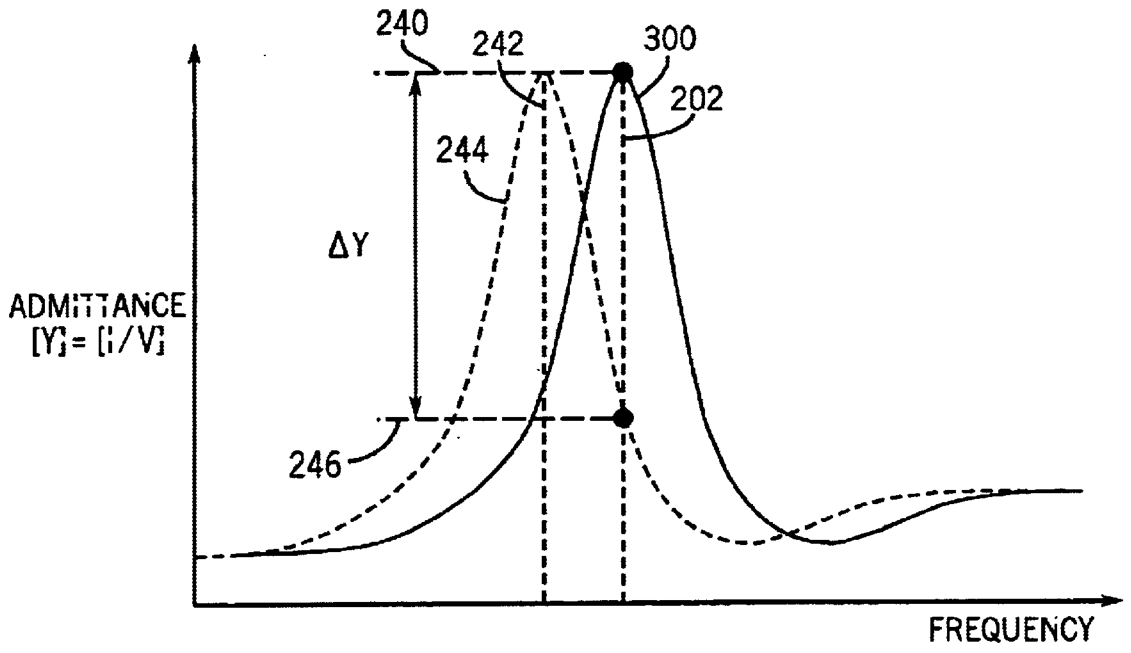
FIGS. 8*a* and 8*b* are graphs illustrating electrical properties of the transducer of FIG. 6*a* that can be used to measure gas pressure magnitude and gas flow direction.

The characteristics described above are used to detect pressure changes and to measure pressures in the breathing circuit in the following manner. For explanatory purposes, FIG. 8*a* shows a simple admittance-frequency curve 300, similar to that shown in FIG. 6*a*. It will be appreciated that the actual admittance-frequency curve for a nebulizer 1 will more generally resemble that of FIG. 6*b* since piezoelectric element 56 is coupled to plate 50 to form a composite pressure transducer structure. Piezoelectric element 56 is energized at resonance frequency 202.

Figure 7A:
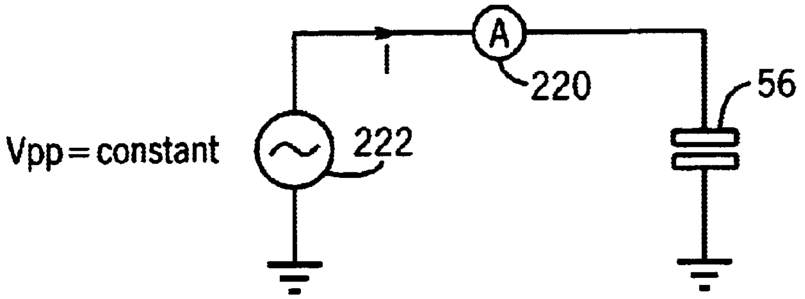
FIGS. 7*a*, 7*b*, and 7*c* are schematic circuit diagrams showing three different techniques for measuring electrical properties of a piezoelectric element to produce data of the type shown in FIGS. 6*b* and 6*c;*
Figure 7B:
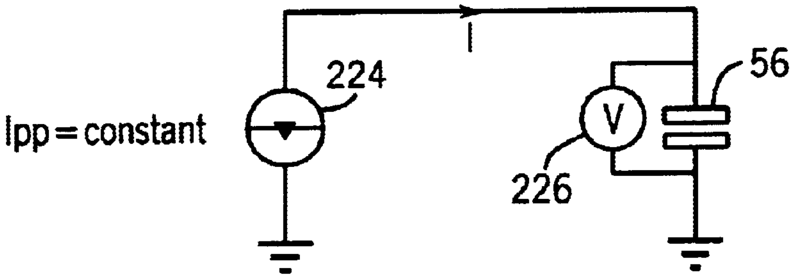
Figure 7C:
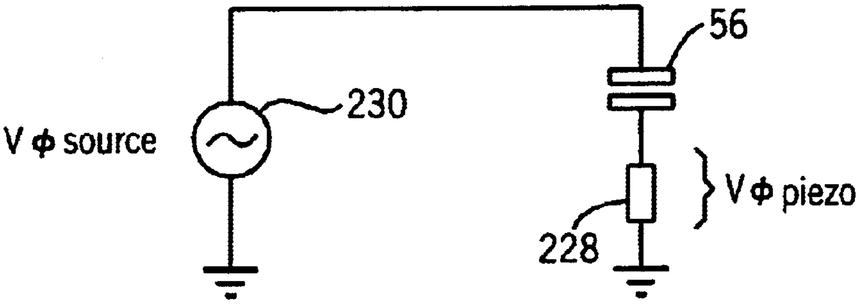
Figure 9:
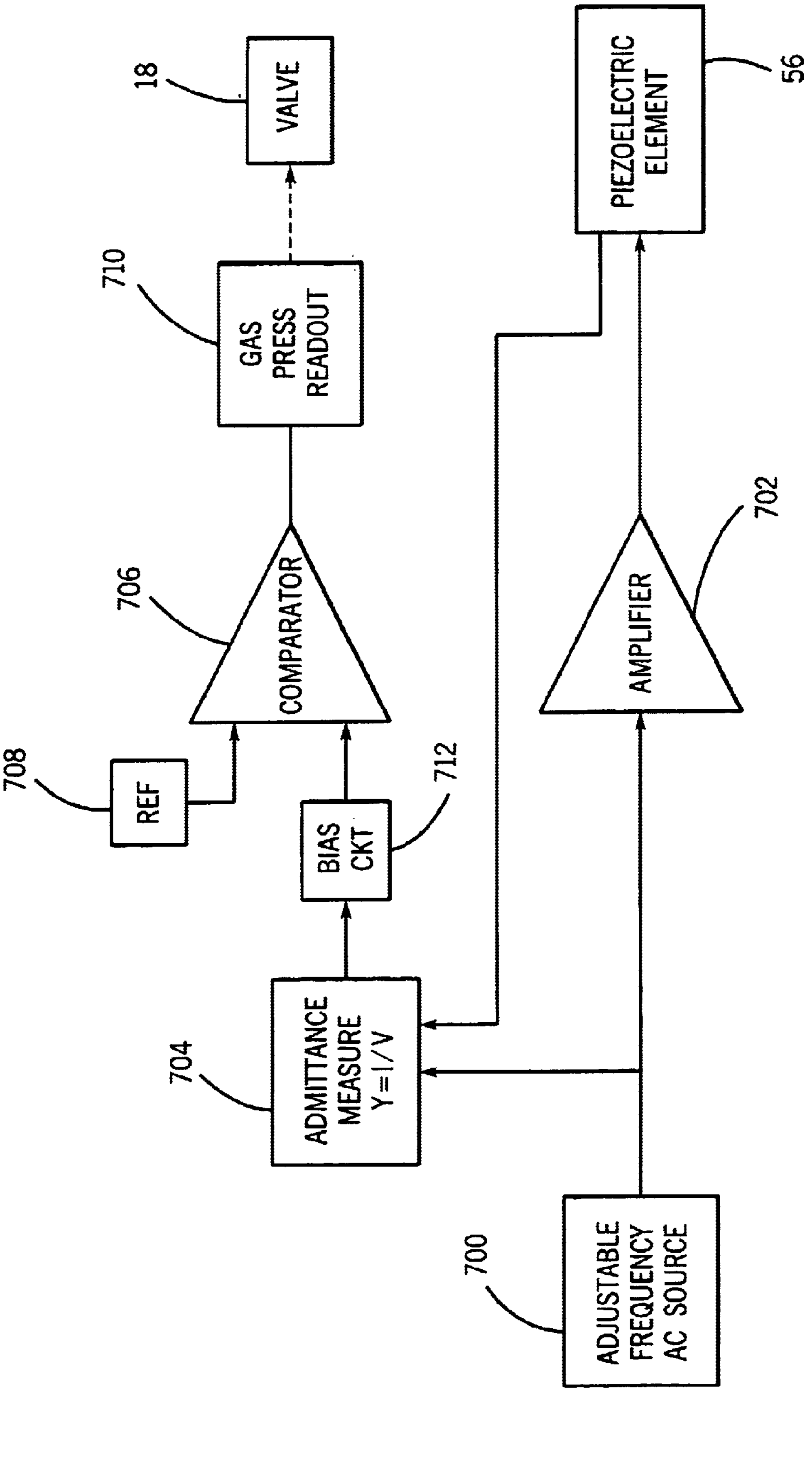
FIG. 9 is a schematic diagram of one embodiment of a circuit suitable for use in the fluid discharging apparatus of the present invention.

FIG. 9 shows a simple circuit that can be incorporated in control 4 and used to energize piezoelectric element 56 at resonance frequency 202. Other suitable circuits are shown in more detail in FIGS. 10 and 12. The circuitry includes an adjustable frequency voltage source 700, such as a voltage controlled oscillator. The output of source 700 may be provided through amplifier 702 to piezoelectric element 56 to energize the element. The admittance of piezoelectric element is measured, as by one of the techniques shown above in connection with FIG. 7, as schematically shown by circuit 704 in FIG. 9.

For example, a current signal may be supplied to circuit 704 for use in conjunction with a voltage signal from source 700 to determine admittance. In FIG. 8*a*, the measured admittance with the composite pressure transducer structure in the unloaded state is shown as level 240. This level is used to establish a reference signal from reference signal source 708 to comparator 706.

As shown in FIGS. 4 and 5, as the subject is ventilated by ventilator 3 or breathes spontaneously, pressure will be applied to plate 50 of nebulizer 1 by the breathing gases in breathing circuit 2. These pressures will, in turn, be applied to piezoelectric element 56. The mechanical loading applied to piezoelectric element 56 will cause the resonance frequency of the piezoelectric pressure transducer structure to shift from frequency 202 to frequency 242, as shown on in FIG. 8*a* by graph 244. The direction of the shift will depend on the construction of the piezoelectric pressure transducer structure and on whether the mechanical load applied to piezoelectric element 56 is tensile or compressive. With the admittance curve shifted to that shown by graph 244, the admittance Y of the pressure transducer structure measured at the energization frequency 202 and determined by circuit 704 will fall to the level 246. The difference in admittance between level 240 and level 246 as determined by comparator 706 is an indication of the pressure change and a measure of the breathing gas pressure in breathing circuit 2 which can be indicated by gas pressure readout circuit 710.

The peaking nature of the graph shown in FIG. 8*a* at the resonance frequency is useful in providing difference values of a magnitude that assists in accurately determining breathing gas pressures. The output of comparator 706 may also be used to operate valve 18 to control the supply of liquid to mesh plate 52 for nebulization in synchronization with specific pressure conditions, such as those indicative of inhalation by the subject. Valve 18 is opened to commence nebulization and thereafter closed. Nebulization stops when the liquid supplied to mesh plate 52 is exhausted.

It will be appreciated that gas pressures in breathing gas circuit 2 continuously vary over most of the respiratory cycle as the subject inspires and expires. Thus, comparisons can also be made in which the fall/rise time and/or the duration of fall/rise of the breathing gas pressure signal are compared to one or several previously measured values and the change or the difference between the values is compared to some predetermined value. In that case, the comparison of the breathing gas pressure signal is based on a differential signal and, for example, drift or slow disturbances have a limited effect on the action used to initiate activation of value 18 or initiate some other operation in nebulizer 1.

Further, the frequency of the electrical energization supplied to the piezoelectric pressure transducer structure by adjustable frequency source can be varied to determine whether the resonance frequency has shifted to a value higher or lower than frequency 202. In the example shown in FIG. 8*a*, as the frequency of the electrical energization is lowered toward frequency 242, the measured admittance value will increase along the right hand slope of graph 244 from the level 246 to a peak value corresponding to level 240, indicating that the resonance frequency has shifted to a lower value. The construction of the pressure transducer containing piezoelectric element 56 will determine whether this frequency shift to a lower value indicates that the loading on the piezoelectric pressure transducer structure is that produced by a breathing gas pressure increase or that produced by a breathing gas pressure decrease.

Or, if the frequency of the electrical energization is increased, the measured admittance value will decrease since the frequency has been moved away from the resonance frequency. This also indicates that the resonance frequency has shifted to a lower value.

Figure 8B:
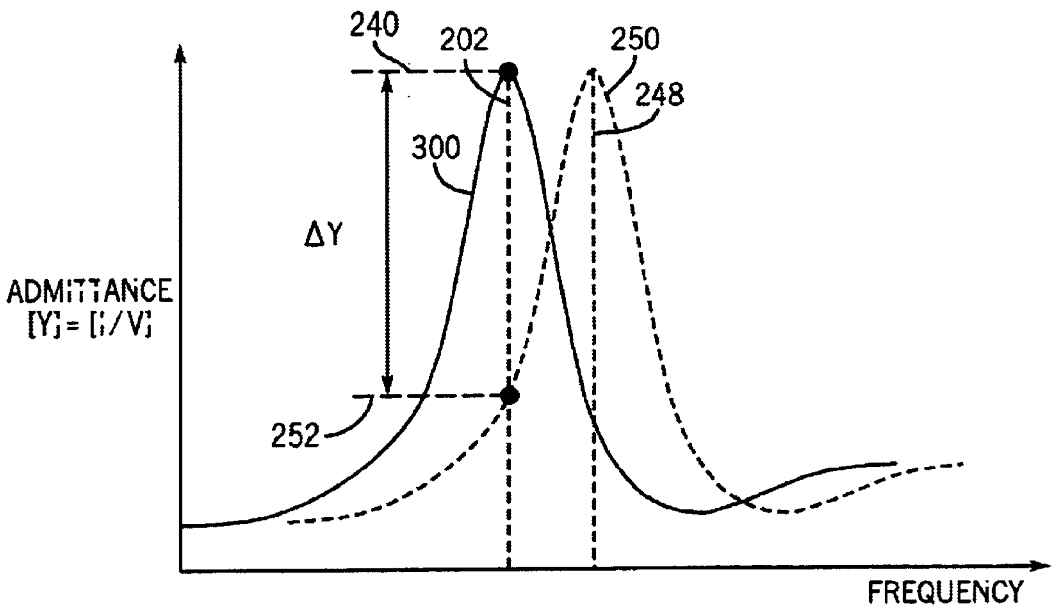

FIG. 8*b* shows the situation in which the pressure applied to plate 50 by the breathing gases in breathing circuit 2 results in a loading of piezoelectric element 56 that causes the resonance frequency to increase, as shown in the figure by frequency 248 and curve 250. The admittance value Y measured at frequency 202 falls to a level 252 lower than level 240 to provide a difference value from comparator 706 that may be used to determine breathing gas pressure in breathing circuit 2. By altering the frequency of the electric energization for piezoelectric element 56, the direction of the shift can be determined by the change in admittance values in the manner described above to confirm the nature of the mechanical loading on the piezoelectric pressure transducer structure.

While FIGS. 8*a* and 8*b* have described operation of nebulizer 1 using resonance frequency 202, it will be appreciated that the breathing gas pressure measuring technique described above will also work should nebulizer 1 be operated at a frequency other than the resonance frequency. The difference in admittance Y values between the unloaded and loaded states of the piezoelectric transducer structure will tend be less than those obtained through the use of the resonance frequency 202 and shown in FIGS. 8*a* and 8*b*.

Also, it will be appreciated that the flow of liquid onto the vibrating mesh plate 52 from valve 18 also temporarily affects the piezoelectric pressure transducer structure as a mechanical load and thus also acts to shift the resonance frequency, such as frequency 202. However, in a simple circuit such as shown in FIG. 9, appropriate compensation can be provided in the determination of admittance Y, as by a bias or offset value circuit 712, to accommodate the effect of the column of liquid between valve 18 and mesh plate 52. Or, in a preferred embodiment of the invention, by periodically adjusting the magnitude of the alternating energization to piezoelectric element 56, atomization may occur at certain times and pressure measurement may take place at other times, as shown and described in more detail in connection with FIGS. 10 and 11.

Figure 8C:
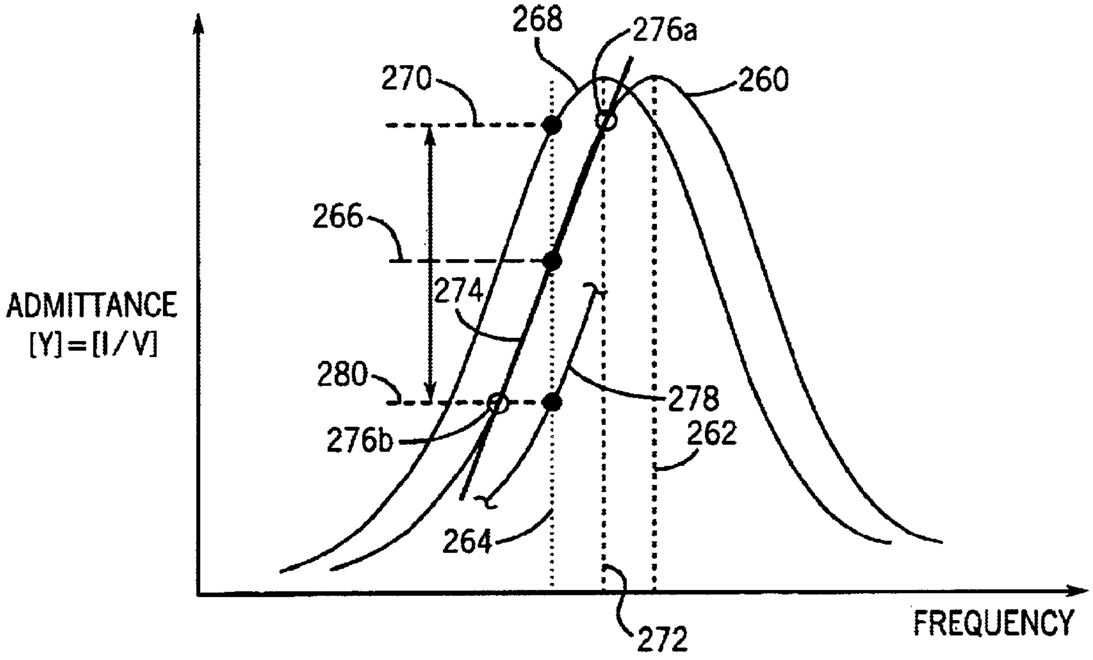
FIG. 8*c* is a graph illustrating another technique for such measurements.

Another technique to measure gas pressure magnitude and flow direction of breathing gas flow is shown in FIG. 8*c*. In this technique, the characteristics of admittance versus frequency, shown graphically in FIG. 8*c* as curve 260, are determined for a state in which the piezoelectric pressure transducer structure is not subject to any mechanical loading. The graph will exhibit a resonance frequency 262.

Nebulizer 1 is then operated to supply electrical energization to piezoelectric element 56 at a frequency 264, different from frequency 262 and the admittance Y for the unloaded state is measured, as level 266 which value is used by reference signal source 708 to provide a reference input to comparator 706.

Thereafter, the piezoelectric pressure transducer structure is subjected to the breathing gas pressures in breathing circuit 2. The mechanical loading applied to piezoelectric element 56 by the breathing gas pressure will shift the admittance-frequency curve, as shown in FIG. 8*c* by graph 268. This shift will cause the admittance of the piezoelectric pressure transducer structure measured at frequency 264 to change to the value indicated by level 270. The change in admittance value can be used by comparator 706 to determine the pressure of the breathing gas in breathing circuit 2.

The fact that the level 270 is greater than admittance level 266 indicates that the resonant frequency has shifted to a lower value. That is, the resonance frequency has shifted from that indicated by frequency 262 for graph 260 to that indicated by frequency 272 for graph 268. This fact can then be used to indicate whether the loading on piezoelectric element 56 applied by plate 50 is tensile or compressive. As noted in FIGS. 4*a* and *b* and 5*a* and b whether the loading is tensile or compressive depends on whether the patient is being mechanically ventilated or is breathing spontaneously and the direction of gas flow in patient limb 10. Knowing the breathing mode for the patient and the type of loading exerted on piezoelectric element 56, the direction of gas flow in patient limb 10 can be determined.

The frequency 264 used for measuring purposes can be chosen in accordance with the construction of the piezoelectric pressure transducer structure and the minimum and maximum gas pressures to be measured. It is usually spaced tens or hundreds of hertz greater or lower than the resonance frequency 262. Also, it is desirable to select a frequency 264 that lies in a generally linear portion of graph 260 for the range of gas pressures to be measured. This provides linearity in the measurement of gas pressure within the pressure range. A linear portion of curve 260 is shown by line 274 and dots 276*a* and 276*b*.

When the mechanical loading applied to piezoelectric element 56 by the breathing gas pressure on plate 52 is opposite to that described above, the admittance versus frequency curve will shift in the opposite direction from that described above. This is shown by the partial curve 278 in FIG. 8*c*. In this circumstance, the admittance value Y measured at frequency 264 will decrease to level 280. The difference between the admittance value 266 and the admittance value 280 may be used by comparator 706 to determine the pressure of the gas in breathing circuit 2. The fact that the admittance value 280 is decreased from admittance value 266 indicates that the loading on piezoelectric element 56 is opposite that which produces admittance level 272. As noted above, this information can be used to determine the direction of gas flow in breathing circuit 2.

While FIG. 8*c* shows operation of nebulizer 1 at a frequency 264 less than resonance frequency 262, it will be appreciated that nebulizer 1 may be operated in an analogous manner for a frequency greater than frequency 262. The changes in admittance caused by a compressive loading of piezoelectric element 56 and a tensile loading of the piezoelectric element will be opposite to that described above in connection with FIG. 8*c*.

A benefit achieved in measuring the breathing gas pressure at a frequency point aside from the natural resonant frequency point is lower power consumption. However, to ensure that the admittance measurements are sufficient to measure pressure changes with the desired degree of accuracy, the amplitude of alternating voltage supplied to the piezoelectric element 56 must be sufficiently high to provide the desired signal to noise the ratio in the signals used for measurement.

By detecting the direction and pressure of the breathing gas flow in breathing circuit 2 using the electric characteristics of the element 56 as described above, and providing this information to control unit 4 it is possible for the control unit 4 to initiate and halt the atomization of the drug to coincide with the breathing of the subject in the manner described generally and schematically above in connection with FIG. 9. This allows the drug to be introduced into the breathing circuit 2 at those moments when the drug can be delivered most effectively through breathing circuit 2 to the subject. Typically, the discharge of liquid into the breathing gas is preferably carried out either during, or partly during, inspiration. If the atomized liquid is dispensed into the breathing circuit 2 only within certain periods during the time the subject is inspiring, the pressure measurement may be carried out only at the beginning of inspiration and during or partly during expiration to find the leading edge of the breathing gas pressure change that characterizes inspiration. This is utilized as the trigger for the start of atomization of the liquid by nebulizer 1. Such a drug delivery technique can provide both an effective drug administration and conserve power in the operation of nebulizer 1. If atomized liquid is dispensed at all times during inspiration, the pressure measurement may be carried out throughout the nebulization to find the leading edge of the breathing gas pressure change that characterizes inspiration to start the atomization and trailing edge of the breathing gas pressure change to stop the atomization.

While FIGS. 8*a*, 8*b*, and 8*c* show comparison of the admittance at the shifted resonance frequency to the admittance at the original resonance frequency, the former admittance value can be compared to a predetermined reference value, if desired, in a manner analogous to that hereinafter described in connection with FIG. 15 to control the operation of nebulizer 1. Or, a given measured admittance value can be compared with a previously measured admittance value, or to an average of previously measured values, to determine a value difference. The value difference is then compared to a reference value to indicate pressure characteristics of the breathing gases and/or control the operation of nebulizer 1.

Figure 10:
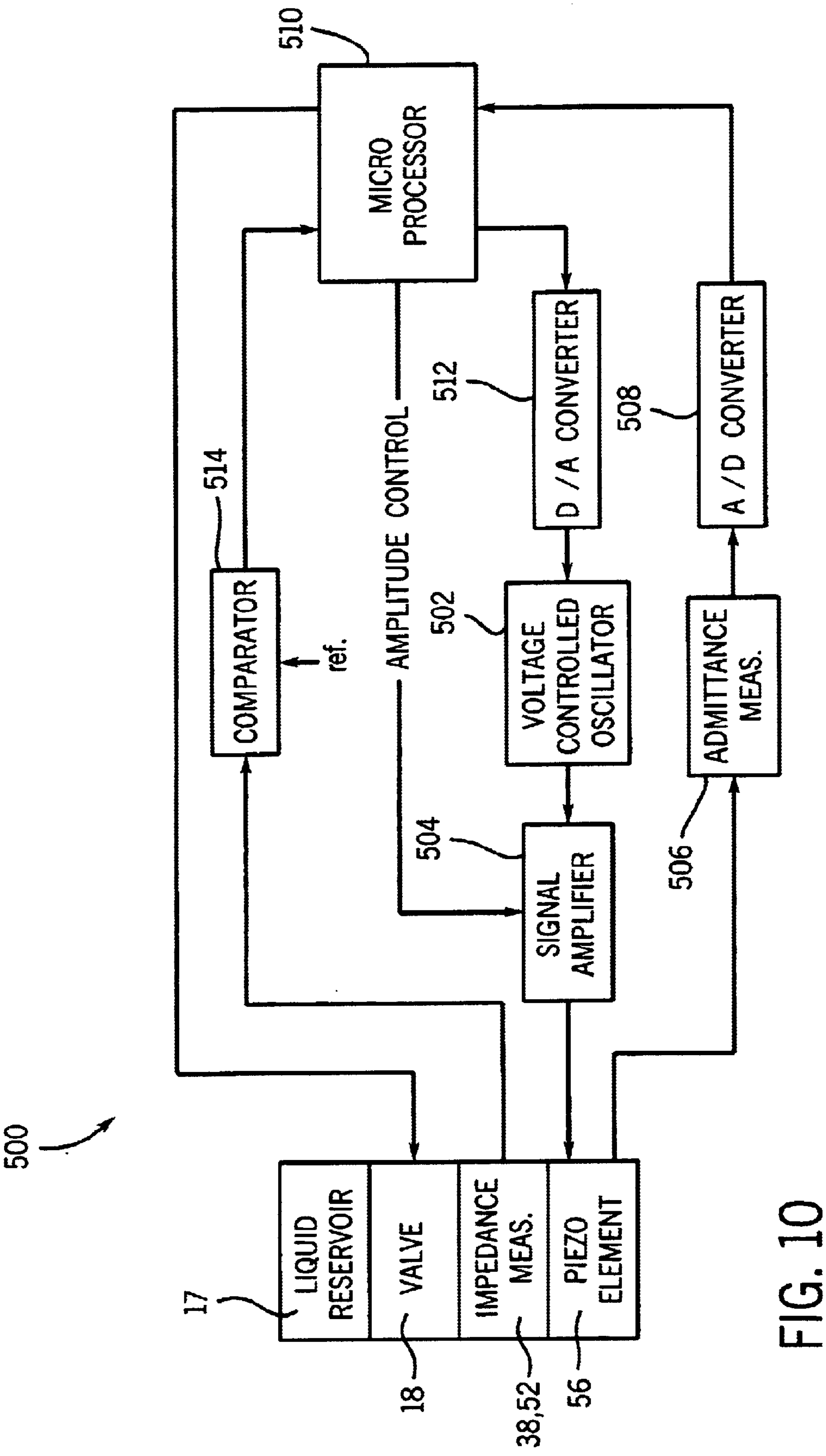
FIG. 10 is a further schematic diagram of circuitry suitable for use in the fluid discharging apparatus of the present invention.

FIG. 10 shows a further embodiment of a control apparatus 500 suitable for use in the nebulizer apparatus and method of the claimed invention. Voltage controlled oscillator 502 provides an adjustable frequency voltage through signal amplifier 504 to piezoelectric element 56 in nebulizer 1. The admittance of piezoelectric element 56 is measured, by one of the techniques/means described above in circuitry 506 and provided through analog/digital converter 508 to microprocessor 510. To determine the resonance frequency of the composite transducer containing piezoelectric element 56, microprocessor 510 operates voltage controlled oscillator 502 through digital/analog converter 512 to scan a predetermined frequency range in which the resonance frequency point should be found. The admittance of piezoelectric element 56 is measured by element 506 during the scanning to determine the peak value of the admittance that indicates the resonance frequency. The resonance frequency is stored in a memory in microprocessor 510. After the resonance frequency is found, microprocessor 510 operates voltage controlled oscillator 502 to provide alternating voltage energization of the resonance frequency, or another desired operating frequency.

After the operating frequency for piezoelectric element 56 has been established, microprocessor 510 operates valve 18 to provide liquid to mesh plate 52. As described above, an impedance measurement is carried out using mesh plate 52 and electrode 38. The impedance measurement signal is provided to comparator 514. The amount of liquid provided by valve 18 may be controlled by a reference signal to comparator 514. The output signal from comparator 514 is provided to microprocessor 510 to operate valve 18.

During operation of nebulizer 1, the impedance measurement detects when the column of liquid supplied to mesh plate 52 is reduced or disappears due to the atomization of liquid through the mesh plate. The signal from comparator 514 causes microprocessor 510 to open valve 18 to resupply liquid until the impedance measurement detects that a sufficient quantity is again present in nebulizer 1 and the above described control loop continues to function in the foregoing manner during operation of nebulizer 1.

During the atomization of the liquid, the liquid on rear surface mesh plate 52 is forced through holes 53 in mesh plate 52 to front surface 54. The motion of mesh plate 52 must exceed the cohesive forces of the liquid being atomized in order to discharge atomized liquid from front surface 54. To ensure the amplitude of vibration of mesh plate 54 is sufficient to cause atomization of the liquid, the amplitude of vibration may be controlled through signal amplifier 504 to alter the amplitude of the alternating voltage applied to piezoelectric element 56. Beneath a certain piezoelectric element voltage excitation amplitude, and corresponding mesh plate 52 vibration magnitude, the atomization of liquid will cease. This means that by reducing the amplitude of the alternating voltage excitation to piezoelectric element 56 to a level below that at which atomization occurs, the composite transducer incorporating piezoelectric element 56 may be used for pressure measurement in the manner described above.

One way in which the foregoing may be carried out is shown in FIG. 11 for a case in which a subject is being mechanically ventilated by ventilator 3.

Figure 11A:
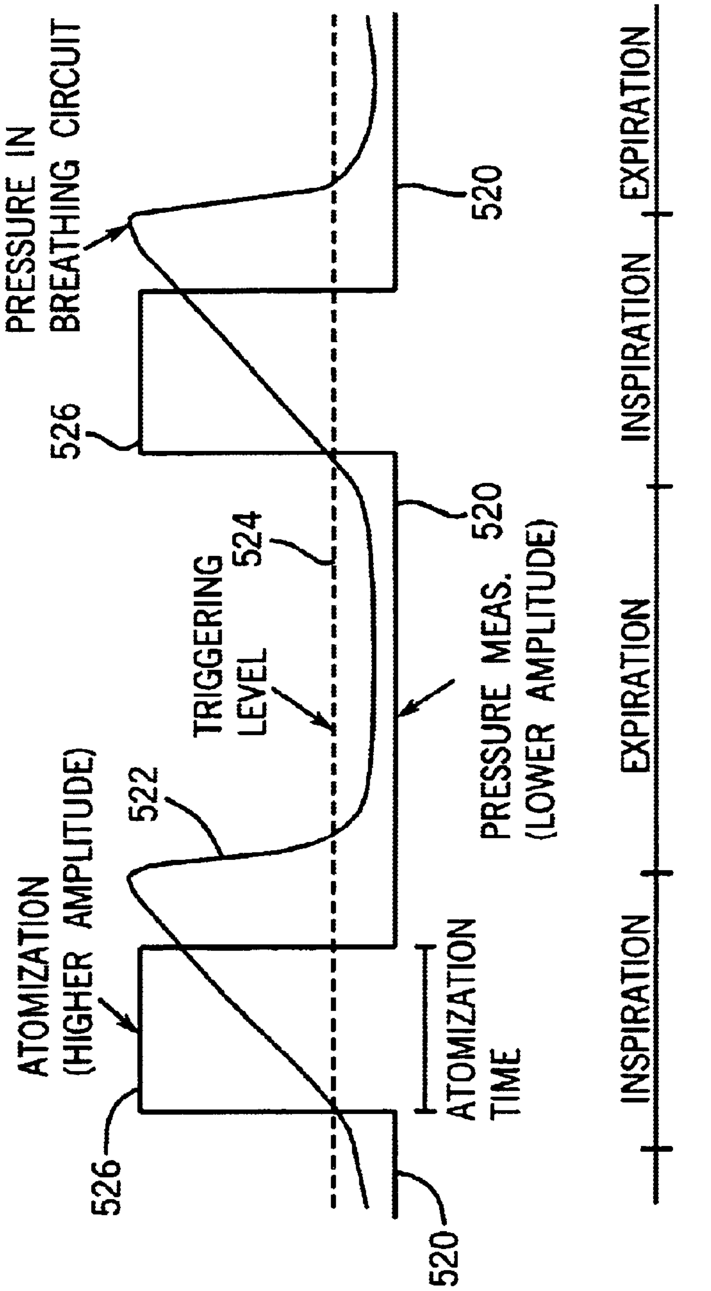
FIGS. 11*a* and 11*b* are graphs showing operation of the circuitry of FIG. 10.

The voltage excitation level for piezoelectric element 56 provided by amplifier 504 is shown at the left side of FIG. 11*a* as at a lower amplitude level 520. Level 520 is sufficiently low that atomization of the liquid does not occur in nebulizer 1. Measurement of the pressure of the breathing gases in breathing circuit 2 is carried out by the composite pressure transducer in the manner described above using microprocessor 510. The microprocessor may provide a readout of gas pressure magnitude. As, the subject is being ventilated by mechanical ventilator 3, the pressure of the breathing gases will rise as the inspiration phase of the breathing cycle is commenced, as shown by graph 522. When the pressure of the breathing gases exceeds a predetermined triggering level 524 established in microprocessor 510, microprocessor 510 operates signal amplifier 504 to increase the amplitude of the voltage excitation to piezoelectric element 56 to a higher amplitude level 526. Excitation amplitude level 526 is sufficient to cause atomization of the liquid to occur in nebulizer 1.

After a predetermined time, and no later than the start of expiration, the amplitude of the excitation to piezoelectric element 56 is reduced to level 520, at which time the measurement of the pressure in breathing circuit 2 resumes.

Operation of piezoelectric element 56 in the manner described above is advantageous in that it provides atomized liquid to the breathing gases in the initial portions of the inspiration phase of the respiratory cycle, thereby to ensure that an atomized liquid, such as a drug, will enter the lungs of the subject during inspiration. It is also advantageous in that power consumption by transducer is reduced inasmuch as the higher amplitude energization 526 is used only during atomization.

Figure 11B:
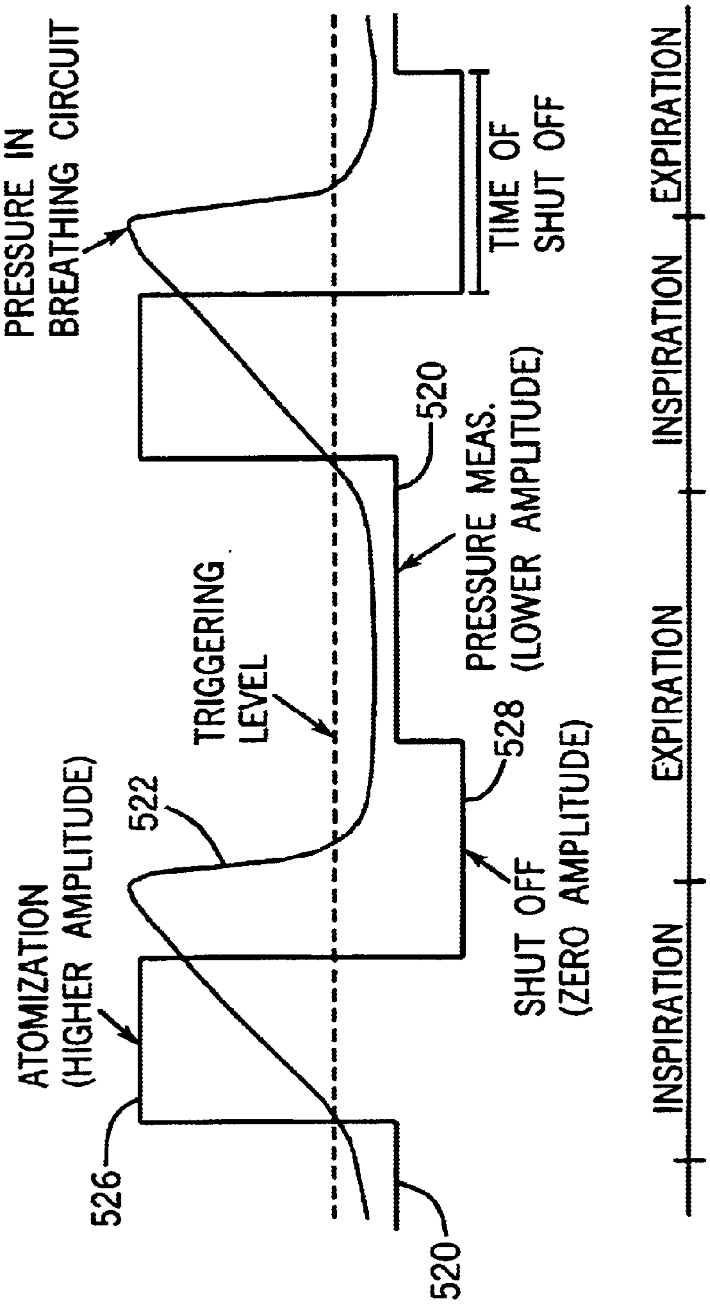

To reduce power consumption even more, the amplitude of the energization for piezoelectric element 56 may be reduced to zero for a predetermined time immediately following the conclusion of the atomization, as shown in FIG. 11*b*. This is shown by signal level 528 in FIG. 11*b*. The energization of piezoelectric element 52 is restored to the low amplitude level 520 as the end of the expiration phase of the subject's respiratory cycle concludes to ensure that proper detection of the leading edge of the inspiratory phase is carried out.

The techniques shown in FIG. 11 have the advantages of reducing power consumption over approaches, such as that shown in FIG. 9, in which the piezoelectric element is continuously operated at a high voltage excitation level.

Figure 12A:
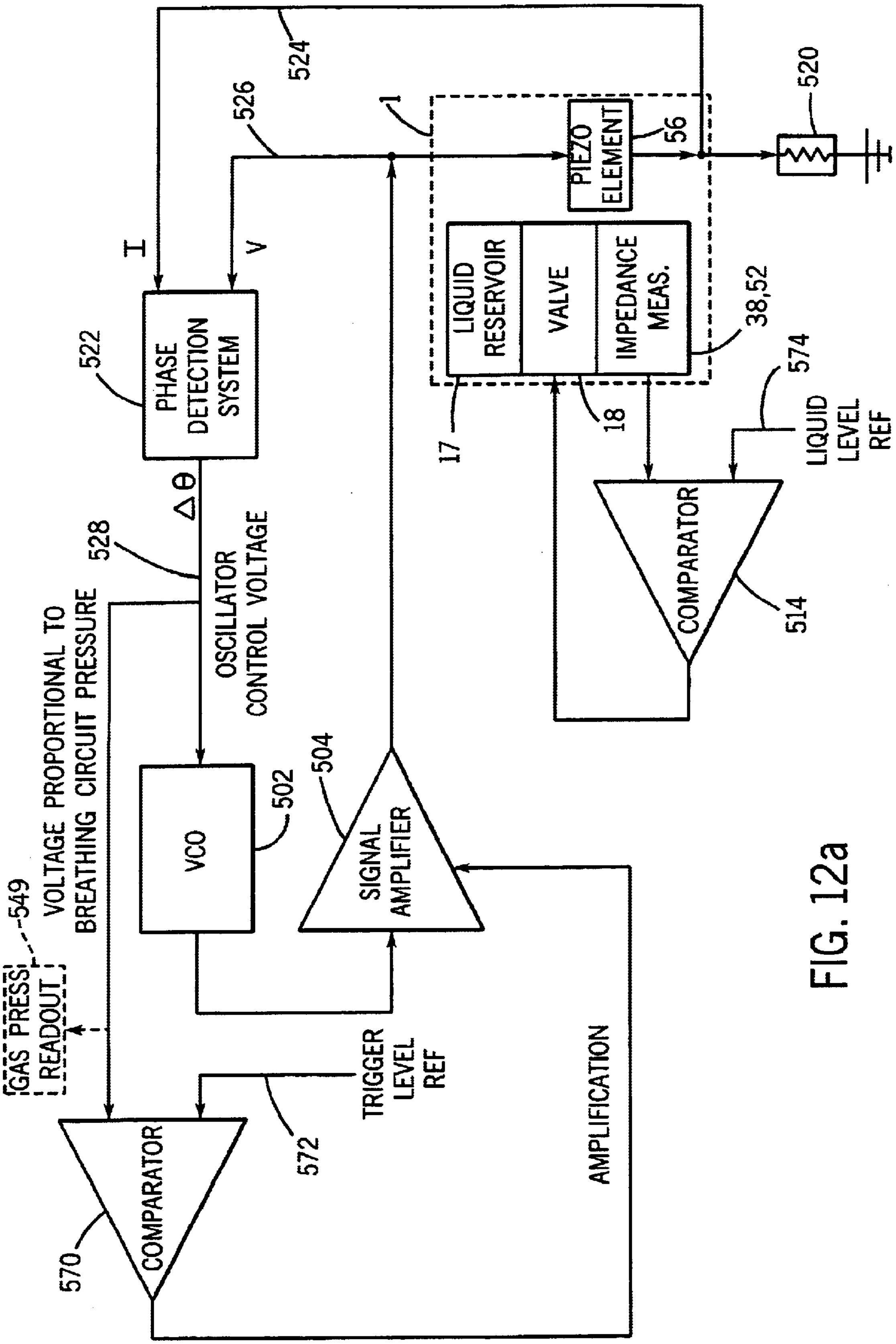
FIGS. 12*a* and 12*b* are a schematic diagram and a graph, respectively, illustrating a further technique for measuring gas pressure magnitude and gas flow direction.
Figure 12B:
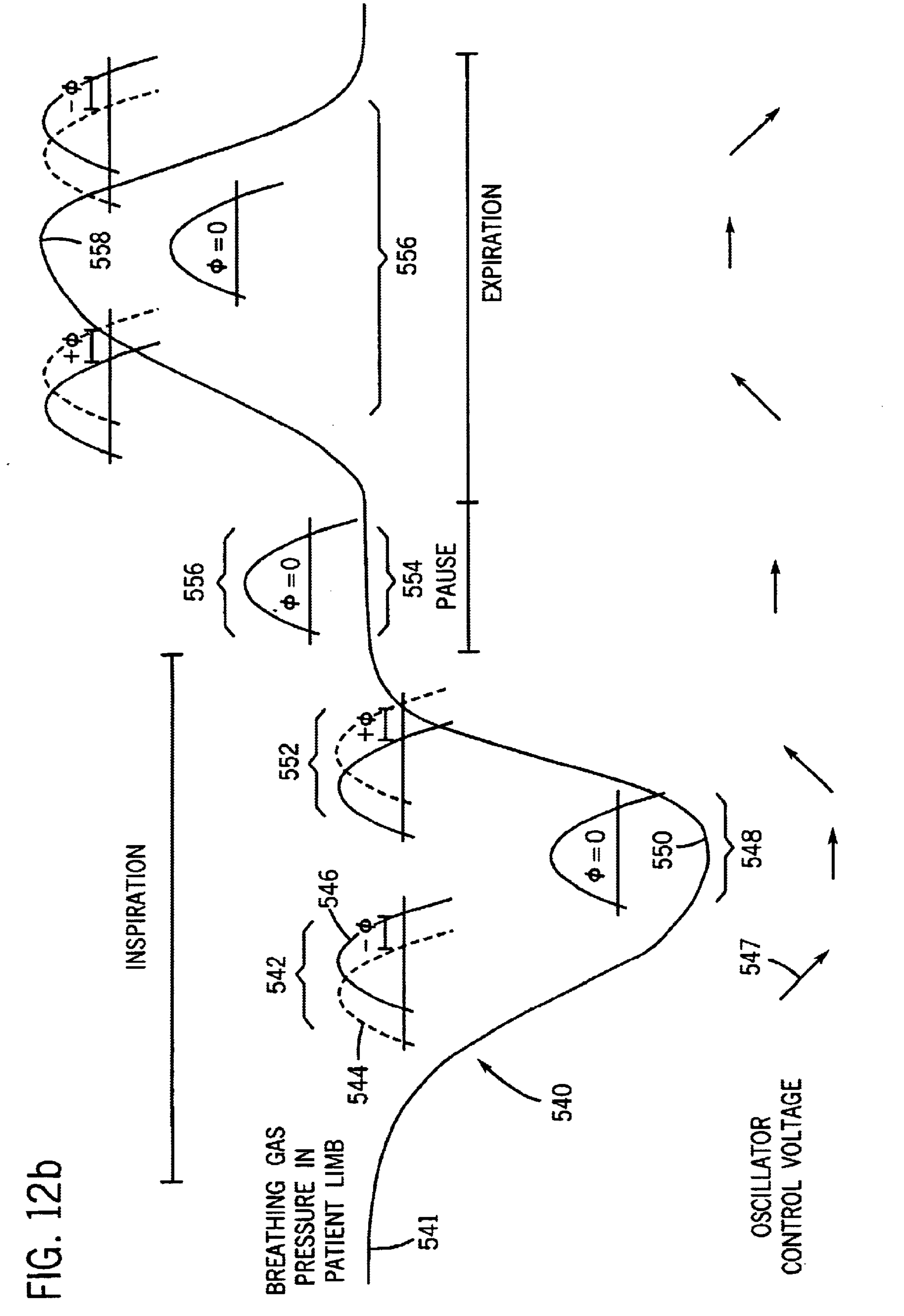

A further technique to measure gas pressure magnitude and flow direction of breathing gas flow is shown in FIG. 12. A circuit for measuring gas pressure magnitude and flow direction based on electrical phase differences between the voltage and current in the composite circuit transducer is shown in FIG. 12*a*. The manner in which the circuit operates is shown in FIG. 12*b*. In FIG. 12*a* components corresponding to those in FIG. 10 are identified by similar reference numerals, it being understood that the circuitry shown in FIG. 12*a* may use appropriate digital signal processing components of the type shown in FIG. 10.

The circuit of FIG. 12*a* includes resistor 520 in series with piezoelectric element 56. Resistor 520 corresponds to resistor 228 shown in FIG. 7*c*. The voltage across resistor 520 is an indication of the current through piezoelectric element 56. The output of signal amplifier 504 containing the amplified output of voltage controlled oscillator 502 is an indication of the voltage applied to piezoelectric element 56. The current signal from resistor 520 and the voltage signal from amplifier 504 are applied to phase displacement detection system 522 in conductors 524 and 526, respectively. Phase detection system 522 determines the phase difference between the two signals, as by detecting zero crossings or some other appropriate technique, and provides a phase difference output signal in conductor 528.

At the resonance frequency of the composite transducer, when there is no mechanical loading on the transducer due to a zero breathing gas pressure or "normal" condition inside patient limb 10, the phase difference between the current and voltage is zero or close to zero.

Gas pressures in patient limb 10 are shown by graph 540 in FIG. 12*b*. The zero breathing gas pressure condition or other baseline condition is shown as 541. For a spontaneously breathing subject, when the subject breathes in at the commencement of inspiration, an underpressure occurs in patient limb 10. This shifts the resonance frequency of the composite transducer, for example, to a lower frequency than the frequency of the output signal of voltage controlled oscillator 502 which is typically at the resonance frequency of the transducer in the zero gas pressure state. These conditions result in a phase difference 542 between the current, as reflected in the signal in conductor 524 measured across resistor 520 and the voltage output of amplifier 504. The phase difference may be one in which the phase of the current 544 is behind the phase of the voltage 546. If the voltage signal 546 is used as a reference, the phase difference may be deemed a "negative" phase difference, i.e. the current lags the voltage.

In the circuit in FIG. 12*a*, this "negative" phase difference is detected by phase detection system 522. Phase detection system 522 then controls voltage controlled oscillator 502 by, for example, decreasing the oscillator control voltage 547 shown in FIG. 12*b* in conductor 528 to alter the frequency of the voltage controlled oscillator to minimize the phase difference. As the oscillator control voltage is decreased, the oscillator output frequency also decreases and the phase difference between the current and the voltage decreases. As the magnitude of negative pressure inside the patient limb stops decreasing at 548, the need to decrease the oscillator control voltage also lessens. Finally, when the negative breathing circuit pressure inside patient limb 10 has reached its minimum value 550, the phase difference again becomes zero, due to the fact that the energization frequency from voltage controlled oscillator 520 has been set to the resonance frequency of the composite transducer at the minimum gas pressure condition. At this point, the oscillator control voltage 547 from phase detection system 522 in conductor 528 is minimum. The change in oscillator control voltage 547 provided by phase detection system 522 is an indication of the breathing gas pressure in patient limb 10 which may be provided as gas pressure readout. The direction of change of the voltage is an indication of the direction flow of the breathing gases in patient limb 10.

As the breathing gas pressure inside the patient limb starts to revert back to its original pressure, as the subject breathes out, the phase difference between the current and the voltage again increases but in the opposite direction, i.e. a "positive" phase difference 552. The new resonance frequency point which was established at breathing gas pressure 550 shifts back to the original resonance frequency as the breathing gas pressure returns to the zero pressure or baseline condition at 554. The "positive" phase difference is detected by phase detection system 522, which then increases the oscillator control voltage 547 for voltage controlled oscillator 502 in conductor 528 toward its original value to again minimize the phase difference between the current and voltage in the composite transducer. As the oscillator control voltage is increased, the oscillator output frequency also increases and the phase difference in the transducer is decreased. As the breathing gas pressure inside patient limb 10 reaches its original value 541, the phase difference becomes minimized, or zeroed, as shown at 556, as the oscillator control voltage and oscillator output frequency reach the same values that established the original zero phase difference.

In the period during which the subject has a pause 554 between inspiration and expiration, the breathing gas pressure inside patient limb 10 remains constant. The phase difference between the current and voltage remains zero and the oscillator control voltage 547 is constant at the nominal potential that establishes the frequency of the energization of piezoelectric element 56 at its original resonance frequency.

When the subject breathes out, during the time interval 556 shown in FIG. 12*b*, the operation of the control circuitry resembles that during inspiration but is now opposite to that described above. This control voltage 547 to voltage controlled oscillator 502 is now increased over the nominal voltage to increase the energization frequency of piezoelectric element 56 to bring about the phase difference minimization at peak positive breathing gas pressure at point 558. As before, the amount and direction of change of oscillator control voltage 547 is an indication of the pressure and flow direction of the breathing gases in patient limb 10.

The oscillator control voltage 547 is controlled by phase detection system 552 as the phase differences occur between the voltage and current in the composite transducer and thus immediately as the breathing gas pressure changes inside patient limb 10. FIG. 12*b* shows the change in oscillator control voltage 547, i.e. the signal in conductor 528 in correspondence with changes in breathing gas pressures in patient limb 10. An upward arrow indicates that the oscillator control voltage is increased, a horizontal arrow indicates that the voltage is constant, and a downward arrow indicates that the voltage is decreased.

In the circuit shown in FIG. 12*a*, the output of phase detection system 522, i.e. the oscillator control voltage 547, which is a voltage proportional to the breathing gas pressure in patient limb 10 also goes to comparator 570. Comparator 570 compares the voltage to a set trigger level voltage in conductor 572 which determines the pressure level for the start of nebulization during inspiration, as described above, in connection with FIG. 11. As noted above, comparisons can also be made in which the fall/rise time and/or the duration of fall/rise of the breathing gas pressure signal are compared to one or several previously measured values and the change or the difference between the values is compared to some predetermined value. In that case, the comparison of the breathing gas pressure signal is based on a differential signal and, for example, drift or slow disturbances have limiting effect on the triggering action provided by comparator 570.

The triggering signal from comparator 570 goes to amplifier 504 and is used to establish the amount of amplification occurring in the energization of piezoelectric element 56 during breathing gas pressure measurement and during nebulization. During breathing gas pressure measurement, the signal level in the amplifier output is adjusted below the signal level used for nebulization, as shown in FIGS. 11*a* and 11*b*. Signal levels may, for example, be adjusted to a 1–100 millivolt range during pressure measurement and to a 1–10 volt range during nebulization.

The supply of liquid from reservoir 17 in nebulizer 1 has its own control loop in the manner described in connection with FIGS. 10 and 11. The impedance sensing means 38, 52 detects the amount of liquid on mesh plate 52. The signal from the impedance sensing means goes to comparator 514 which performs a comparison to a set liquid level reference in conductor 574. If the amount of liquid is less than the set level, valve 18 is open to supply more liquid from reservoir 17 until the desired amount is reached, after which the comparator output closes the valve. The liquid may be supplied to mesh plate 52 only during nebulization so that the load effect on the composite transducer is avoided or minimized during pressure measurement. However, if the liquid supply does have a load effect on piezoelectric element 56 and thus its resonance frequency, the signal from phase detection system 522 can be filtered, biased, or removed whenever the liquid is supplied to mesh plate 52.

FIG. 13*a* shows another embodiment of a structure that can be used to obtain atomization of a liquid in nebulizer 1. In the schematic cross-sectional view of FIG. 13*a*, a bi-morph structure 290 comprises a ring-shaped piezoelectric element 292 attached with adhesive 294 to a disk-shaped metal plate 296. Plate 296 is made of a conductive, generally rigid material, such as brass, having a center hole for the attachment of a mesh plate 298 similar to the mesh plate 52. The bi-morph structure 290 is vibrated in a bending mode illustrated by the dashed line 300 in FIG. 13*a* by an alternating electrical energization applied to the terminals, such as terminals 35 and 36 which contact the structure A liquid is simultaneously supplied to mesh plate 298 and is discharged through the holes in the mesh plate. The bi-morph structure 290 may be used for gas pressure and flow direction measurements in the same manner as plate 50 and element 56 when incorporated in nebulizer 1.

FIG. 13*b* shows a schematic cross-sectional view of another type of a transducer structure 302 that can be employed in nebulizer 1. Structure 302 comprises a ring-shaped piezoelectric element 304 attached with adhesive around the periphery of a disk-shaped plate 306 made of a conductive, generally rigid material, such as brass, having a center hole for the attachment of a mesh plate 308. When an alternating electrical energization is applied to terminals contacting the piezoelectric element 304, the element 304 vibrates in a radial mode as shown by the dotted lines in FIG. 13*b*, with the vibrating force directed to plate 306. The plate 306 then starts to vibrate in a bending mode, as indicated by the dashed line 310 in FIG. 13*b*. Liquid supplied onto one side of mesh plate 308 is then discharged through the holes in the mesh plate. The transducer structure 302 can also be used for gas pressure and flow direction measurements when incorporated, for example, in nebulizer 1 shown in FIG. 2.

FIG. 14 shows an alternative embodiment of a piezoelectric structure for discharging a liquid into a receiving gas. In the structure of FIG. 14, a piezoelectric element in the form of a piezoelectric rod 600 is mounted at one end of elongated housing 602. An outlet 604 is provided at the other end of housing 602. Liquid inlet 606 opens into housing 602 intermediate the ends of the housing. Piston 608 is fastened to piezoelectric element 600.

In operation, when piezoelectric element 600 is supplied with an alternating voltage, piston 608 is reciprocated in housing 602. In a withdrawn state of piston 608, inlet 606 is opened to provide a column of liquid in the lower portion of housing 602. In an extended state of piston 608, liquid is driven from outlet 604 of housing 602 into a receiving gas. The pressure of the receiving gas will be transmitted through the liquid column and piston 608 to piezoelectric element 600 so that resonance frequency and admittance value changes in the piezoelectric element can reflect the pressure and flow direction of the receiving gas. If it is desired to more finely atomize the liquid, appropriate means, such as a mesh plate, may be provided for the liquid discharged from housing 602.

Figure 15A:
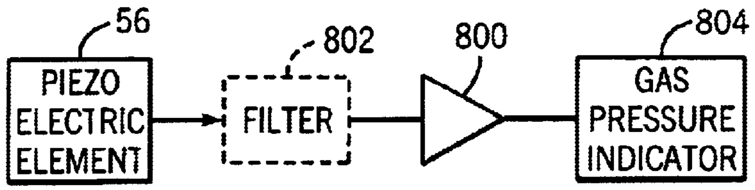
FIGS. 15*a*, 15*b*, and 15*c* are schematic diagrams of simple circuits suitable for use in the fluid discharging apparatus of the present invention.

FIG. 15*a* shows circuitry suitable for use in a passive embodiment of the present invention in which piezoelectric element 56 is not actively energized as by source 700. Rather, the voltage appearing at the terminals of transducer 68, as element 56 is subjected to mechanical loading by member 50, is measured and used as an indication of the pressure of the receiving gas. For this purpose, piezoelectric element 56 is connected to the input of amplifier 800. The output of the piezoelectric element may be filtered by filter 802, if desired, to remove noise and to provide a bandpass for signals having desired frequency characteristics. The output of amplifier 800 is provided to gas pressure indicator 804. Changes in the output of amplifier 800 may be used to detect the commencement of the inspiratory phase of the patient's respiratory cycle to cause the nebulizer to provide atomized fluid to the breathing gases.

Figure 15B:
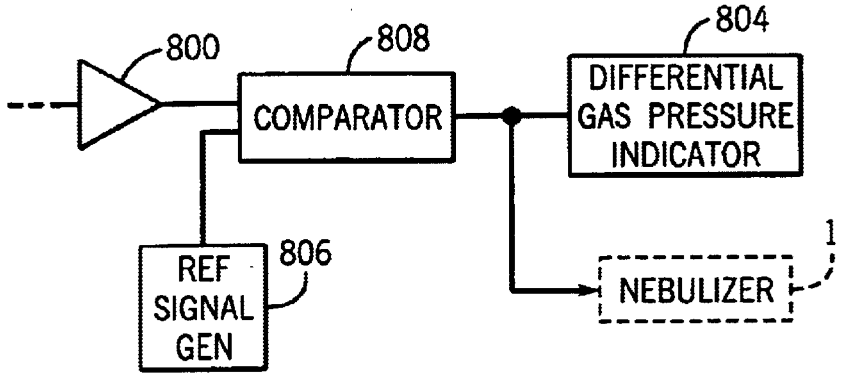
Figure 15C:
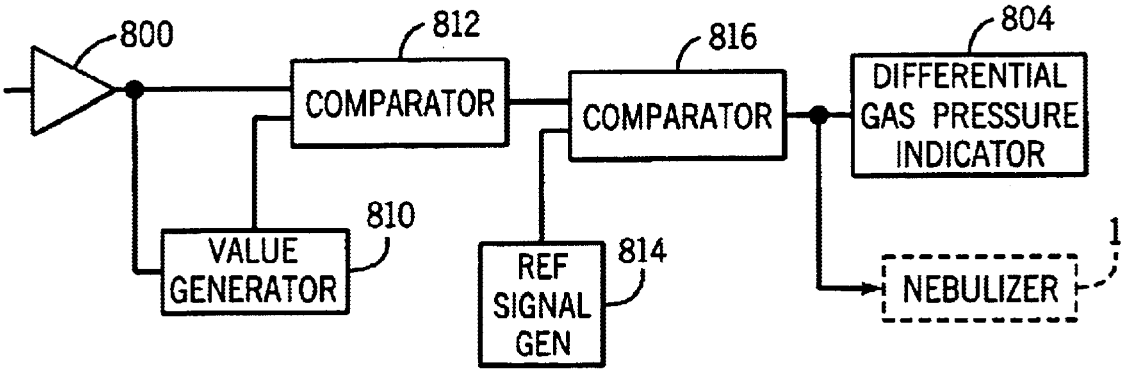

To detect gas pressure changes to carry out a triggering action and/or to provide an indication of gas pressure, the output of amplifier 800 may be compared to a predetermined reference value from reference value generator 806 in comparator 808 shown in FIG. 15*b*. The output of comparator 808 provides a differential gas pressure measurement at indicator 804 and/or operates nebulizer 1. Or, the measured value may be compared to some other reference value, such as a previously measured value or an average of previously measured values produced by value generator 810 shown in FIG. 15*c*. The difference between the two values determined by comparator 812 is then compared to a predetermined reference quantity from reference value generator 814 in comparator 816 for us in controlling the operation of the nebulizer or as an indication of gas pressure.

It will be appreciated that the frequencies present in the embodiment of the invention shown in FIG. 15 will be much lower than those found in the active embodiments of the invention, described above. That is, the signal frequencies will tend to be those of the subject's respiratory rate. The same is true of the output signal levels and the amounts by which the signal levels change in the course of operating of the liquid discharging apparatus. Output signal levels, and changes therein can be enhanced by mechanically "tuning" the transducer to a resonance frequency corresponding to that of the mechanical loading to which it is subjected. This may be accomplished by appropriate selection of the physical characteristics of element 56 and member 50 and/or the composition of these elements.

The embodiment of the invention shown in FIG. 15 provides an economical version of the present invention but having somewhat less accuracy in gas pressure measurement.

Various other types of elements that function in the same manner as the foregoing could also be substituted for those described in detail, above. Thus, it is recognized that other equivalents, alternatives, and modifications aside from those expressly stated, are possible and within the scope of the appended claims.

What is claimed is:

1. A method for use with a discharging means discharging a fluid substance into a receiving gas, said method determining the pressure of the receiving gas, said method comprising the steps of:

(a) placing the discharging means in fluid communication with the receiving gas so that a bidirectional mechanical-electrical conversion element is subjected to mechanical loading responsive to the gas pressure of the receiving gas, the element mechanically vibrating responsive to the application of alternating electrical energization to the element, the element having an admittance, the admittance of the element at a given frequency of alternating electrical energization being alterable by a mechanical loading of the element;

(b) applying alternating electrical energization to the element at a selected frequency;

(c) subjecting the element to mechanical loading responsive to the pressure of the receiving gas;

(d) measuring the admittance exhibited by the element in the loaded condition when energized by the electrical energization of the selected frequency; and (e) determining the difference between the admittance measured in step (d) and another value as an indication of the pressure of the receiving gas.

2. The method of claim 1 wherein a pressure transducer comprising said element has a resonance frequency at which the admittance of the element has a peak value and wherein step (b) is further defined as applying alternating electrical energization to the element at the resonance frequency.

3. The method of claim 1 wherein a pressure transducer comprising said element has a resonance frequency at which the admittance of the element has a peak value and wherein step (b) is further defined as applying alternating electrical energization to the element at a frequency other than the resonance frequency.

4. The method of claim 1 wherein step (c) is further defined as subjecting a member to pressure exerted by the receiving gas, the member exerting a mechanical loading on the element responsive to the gas pressure.

5. The method of claim 4 wherein step (c) is further defined as subjecting a member comprising a porous plate, through which fluid is discharged into the receiving gas by the vibratory action of the element, to the pressure exerted by the receiving gas.

6. The method of claim 4 wherein step (c) is further defined as subjecting a member comprising a piston for discharging fluid into the receiving gas by the vibratory action of the element to the pressure exerted by the receiving gas.

7. The method of claim 1 wherein the bidirectional mechanical-electrical conversion element of the fluid discharging means comprises a piezoelectric element.

8. The method of claim 7 wherein step (c) is further defined as exerting the mechanical loading on the piezoelectric element along an axis of vibration of the piezoelectric element.

9. The method of claim 7 wherein the piezoelectric element is a ring-like piezoelectric element coupled to said member and wherein step (b) is further defined as applying alternating electrical energization to the element to cause bowing in the member and wherein, in step (c), the pressure of the receiving gas applied to the member also causes bowing of the member.

10. The method of claim 4 wherein the bidirectional mechanical-electrical conversion element of the fluid discharging means comprises a bi-morph structure.

11. The method of claim 10 wherein said element is a ring-like element and wherein step (b) is further defined as applying alternating electrical energization to the element to cause bowing in the member and wherein, in step (c), the pressure of the receiving gas applied to the member also causes bowing of the member.

12. The method of claim 7 wherein the piezoelectric element is a rod-like element for reciprocating a piston in a fluid filled housing.

13. The method of claim 1 further including a step (f) of measuring the admittance exhibited by the element in an unloaded condition when energized by the electrical energization of the selected frequency and wherein step (e) is further defined as measuring the difference between the admittance measured in steps (f) and (d) as an indication of the pressure of the receiving gas.

14. The method of claim 1 wherein step (e) is further defined as determining the difference between the admittance measured in step (d) and a reference value to obtain the indication.

15. The method of claim 14 wherein step (e) is further defined as determining the difference between the admittance measured in step (d) and a value derived from previously measured admittance values obtained in the manner of step (d), and wherein the difference so determined is compared to a reference value to obtain the indication.

16. The method of claim 1 wherein step (d) further comprises the steps of applying alternating electrical energization having a desired voltage property which is constant in magnitude to the element; measuring the current through the element; and determining the admittance exhibited by the element from the voltage property and the measured current value.

17. The method of claim 1 wherein step (d) comprises the steps of applying alternating electrical energization having a desired current property which is constant in magnitude to the element; measuring the voltage across the element; and determining the admittance exhibited by the element from current property and the measured voltage.

18. The method of claim 1 wherein step (d) comprises the steps of measuring the phase shift in the alternating electrical energization as a result of its application to the element and using the phase shift as an indication of the admittance of the element.

19. The method of claim 13 wherein at least one of steps (e) and (f) further comprises the steps of applying alternating electric energization having a desired voltage property which is constant in magnitude to the element; measuring the current through the element; and determining the admittance exhibited by the element from the voltage property and the measured current value.

20. The method of claim 13 wherein at least one of steps (e) and (f) further comprises the steps of applying alternating electrical energization having a desired current property which is constant in magnitude to the element; measuring the voltage across the element; and determining the admittance exhibited by the element from current property and the measured voltage.

21. The method of claim 13 wherein at least one of steps (e) and (f) further comprises the steps of measuring the phase shift in the alternating electrical energization as a result of its application to the element and using the phase shift as an indication of the admittance of the element.

22. The method of claim 1 further defined as a method for measuring the pressure of the breathing gases for a subject.

23. The method of claim 1 wherein the fluid discharging means comprises a nebulizer.

24. The method of claim 22 wherein the fluid discharging means comprises a nebulizer.

25. The method of claim 13 further defined as determining a flow direction of the receiving gas, opposite directions of flow of the receiving gas subjecting the fluid discharging means element to differing pressures and subjecting the element to differing mechanical loading, said method further including the steps of:

(g) altering frequency of the alternating electrical energization applied to the element to a frequency higher or lower than that applied in step (b);

(h) measuring the admittance exhibited by the element in the loaded condition when energized by the electrical energization of altered frequency;

(i) determining the difference in the admittances measured in steps (d) and (h); and (j) comparing the difference determined in step (i) with the difference determined in step (e) to determine the direction of flow of the receiving gas.

26. The method of claim 25 wherein step (b) is further defined as applying alternating electrical energization to the element at a resonance frequency.

27. The method of claim 13 further defined as subjecting a member to pressure exerted by the receiving gas, the member exerting a mechanical loading on the element responsive to gas pressure, said method being further defined as a method for determining the flow direction of the receiving gas, opposite directions of receiving gas flow subjecting the fluid discharging means member to differing pressures and subjecting the element to differing mechanical loading, said method including the steps of:

(g) comparing the admittance measured in step (e) with the admittance measured in step (d) to determine the relative magnitude of the measured admittances; and (h) determining from the relative magnitudes of the measured admittances, the direction of flow of the receiving gas.

28. The method of claim 27 wherein the admittance of the element and the frequency of the applied alternating electrical energization exhibit a linear relationship over a given range of alternating electrical energization frequencies and wherein step (b) is further defined as applying alternating electrical energization to the element at a frequency within the given range.

29. The method of claim 1 further defined as altering the amplitude of the alternating electrical energization applied to the element.

30. The method of claim 29 further defined as altering the amplitude of the alternating electrical energization applied to the element between a low level at which the pressure of the receiving gas is determined and a higher level at which discharge of the fluid substance occurs.

31. The method of claim 22 further defined as including the steps of:

establishing the amplitude of the alternating electrical energization applied to the element at a level below that at which atomization of the fluid substance occurs;

determining the pressure of the breathing gases for the subject;

when the pressure of the breathing gases bears a predetermined relationship to a preselected pressure level, increasing the amplitude of the alternating electrical energization applied to the element to a higher level at which discharge of the fluid substance into the breathing gases occurs; and thereafter reducing the amplitude of the alternating electrical energization applied to the element to the lower level.

32. The method of claim 29 further defined as including the step of removing electrical energy from the element for a period of time.

33. A method for use with a discharging means discharging a fluid substance into a receiving gas, said method determining the flow direction of the receiving gas, said method comprising the steps of:

(a) placing the discharging means in fluid communication with the receiving gas so that a bidirectional mechanical-electrical conversion element is subjected to mechanical loading responsive to the gas pressure of the receiving gas, the element mechanically vibrating responsive to the application of alternating electrical energization to the element, the element having an admittance, the admittance of the element at a given frequency of alternating electrical energization being alterable by a mechanical loading of the element, opposite directions of flow of the receiving gas subjecting the element to differing pressures and exerting differing mechanical loading on the element;

(b) applying alternating electrical energization to the element at a selected frequency;

(c) subjecting the element to mechanical loading responsive to the pressure of the receiving gas;

(d) measuring the admittance exhibited by the element in the loaded condition when energized by the electrical energization of the selected frequency;

(e) altering frequency of the alternating electrical energization applied to the element to a frequency higher or lower than that applied in step (b);

(f) measuring the admittance exhibited by the element in the loaded condition when energized by the electrical energization of altered frequency;

(g) using the relative magnitudes of the admittances measured in steps (d) and (f) and the direction of the frequency shift in alternating electrical energization to determine the nature of the mechanical loading on the element and the direction of flow of the receiving gas.

34. A method for use with a discharging means discharging a fluid substance into a receiving gas, said method determining the flow direction of the receiving gas, said method comprising the steps of:

(a) placing the discharging means in fluid communication with the receiving gas so that a bidirectional mechanical-electrical conversion element is subjected to mechanical loading responsive to the gas pressure of the receiving gas, the element mechanically vibrating responsive to the application of alternating electrical energization to the element, the element having an admittance, the admittance of the element at a given frequency of alternating electrical energization being alterable by a mechanical loading of the element, opposite directions of flow of the receiving gas subjecting the element member to differing pressures and exerting differing mechanical loading on the element;

(b) applying alternating electrical energization to the element at a selected frequency;

(c) measuring the admittance exhibited by the element in an unloaded condition when energized by the electrical energization of the selected frequency;

(d) subjecting the element to mechanical loading responsive to the pressure of the receiving gas;

(e) measuring the admittance exhibited by the element in the loaded condition when energized by the electrical energization of the selected frequency;

(f) comparing the admittance obtained in step (c) with the admittance obtained in step (e) to determine the relative magnitude of the measured admittances; and (g) determining from the relative magnitudes of the measured admittances, the direction of flow of the receiving gas.

35. The method of claim 34 wherein a pressure transducer comprising said element has a resonance frequency at which the admittance of the element has a peak value and wherein step (b) is further defined as applying alternating electrical energization to the element at a frequency other than the resonance frequency.

36. Apparatus for discharging a fluid substance into a receiving gas, said apparatus determining the pressure of the receiving gas, and comprising:

(a) fluid discharging means in fluid communication with the receiving gas, said discharging means having a bidirectional mechanical-electrical conversion element subjected to mechanical loading responsive to the gas pressure of the receiving gas, the element mechanically vibrating responsive to the application of alternating electrical energization to the element, the element having an admittance, the admittance of the element at a given frequency of alternating electrical energization being alterable by a mechanical loading of the element;

(b) means for measuring the admittance exhibited by said element, the admittance exhibited by said element being measured at a selected frequency of alternating electrical energization when said element is subject to a mechanical loading; and (c) means for comparing the measured the admittance of said element when subjected to a mechanical loading with another value to provide an indication of the pressure of the receiving gas.

37. The apparatus of claim 36 wherein said admittance measuring means is further defined as measuring the admittance at a resonant frequency of a pressure transducer including said element.

38. The apparatus of claim 36 wherein said admittance measuring means is further defined as measuring the admittance at a frequency other than the resonant frequency of a pressure transducer including said element.

39. The apparatus of claim 36 wherein said admittance measuring means is further defined as also measuring the admittance of the element in the unloaded condition and wherein said comparing means is further defined as comparing the measured admittance of said element in the unloaded condition and the admittance of the element when subjected to mechanical loading.

40. The apparatus of claim 36 wherein said comparing means is further defined as comparing the admittance of said element to a reference value.

41. The apparatus of claim 40 further including means for deriving a value from a previously measured admittance of said element, wherein said comparing means determines a difference between said measured admittance value and said derived value and wherein said apparatus includes means for comparing the difference to a reference value as an indication of the pressure of the receiving gas.

42. The apparatus of claim 36 further including a member subjected to the pressure of the receiving gas, said member being coupled to said element for mechanically loading said element.

43. The apparatus of claim 42 wherein said member comprises a plate having perforations through which fluid is discharged into the receiving gas.

44. The apparatus of claim 43 wherein said plate has a ring-like bidirectional mechanical-electrical conversion element coupled thereto and surrounding said perforations.

45. The apparatus of claim 42 wherein said member comprises a piston reciprocating in a fluid filled housing for discharging fluid into the receiving gas.

46. The apparatus of claim 36 wherein said element comprises a piezoelectric element.

47. The apparatus of claim 36 wherein said element comprises a bi-morph structure.

48. The apparatus of claim 36 wherein said admittance measuring means comprises means for applying alternating electrical energization having a desired voltage property which is constant in magnitude to the element; means for measuring the current through the element; and means for determining the admittance exhibited by the element from the voltage property and the measured current value.

49. The apparatus of claim 36 wherein said admittance measuring means comprises means for applying alternating electrical energization having a desired current property which is constant in magnitude to the element; means for measuring the voltage across the element; and means for determining the admittance exhibited by the element from current property and the measured voltage.

50. The apparatus of claim 36 wherein said admittance measuring means comprises means for measuring the phase shift in the alternating electrical energization as a result of its application to the element and means employing the phase shift to indicate the admittance of the element.

51. The apparatus of claim 36 further defined as one for measuring the pressure of the breathing gases for a subject.

52. The apparatus of claim 36 wherein the fluid discharging means comprises a nebulizer.

53. The apparatus of claim 51 wherein the fluid discharging means comprises a nebulizer.

54. The apparatus of claim 39 further defined as one for measuring a flow direction of the receiving gas, opposite directions of flow of the receiving gas subjecting the fluid discharging means element to differing pressures and subjecting the element to differing mechanical loading, and wherein said admittance measuring means is further defined as measuring the admittance exhibited by said element in the loaded condition at a frequency higher or lower than said selected frequency; and wherein said comparing means is further defined as employing the relative magnitudes of said measurements to determine the flow direction of the receiving gas.

55. The apparatus of claim 37 further defined as one for measuring a flow direction of the receiving gas, opposite directions of flow of the receiving gas subjecting the fluid discharging means element to differing mechanical loading, wherein said pressure transducer has a resonance frequency at which the admittance of the elements has a peak value, the alternating electrical energization applied to said element being at a frequency other than the resonance frequency, and wherein said comparing means employs the relative magnitudes of said measurements to determine the flow direction of the receiving gas.

56. Apparatus for discharging a fluid substance into a receiving gas, said apparatus determining the flow direction of the receiving gas, and comprising:

(a) fluid discharging means in fluid communication with the receiving gas, said discharging means having a bidirectional mechanical-electrical conversion element subjected to mechanical loading responsive to the gas pressure of the receiving gas, the element mechanically vibrating responsive to the application of alternating electrical energization to the element, the element having an admittance, the admittance of the element at a given frequency of alternating electrical energization being alterable by a mechanical loading of the element;

(b) means for measuring the admittance exhibited by said element, the admittance exhibited by said element being measured at a selected frequency of alternating electrical energization in the unloaded condition, said means measuring the admittance of said element at a frequency higher or lower than the selected frequency when said element is subjected to a mechanical loading; and (c) means for comparing the measured admittance of said element when said element is in the unloaded condition and the admittance of said element when said element is subjected to a mechanical loading to provide an indication of the flow direction of the receiving gas.

57. Apparatus for discharging a fluid substance into a receiving gas, said apparatus determining the flow direction of the receiving gas, and comprising:

(a) fluid discharging means in fluid communication with the receiving gas, said discharging means having a bidirectional mechanical-electrical conversion element, a pressure transducer including said element having a resonance frequency at which the admittance of the element has a peak value, the element being subjected to a mechanical loading responsive to the gas pressure of the receiving gas, the element mechanically vibrating responsive to the application of alternating electrical energization to the element, the element having an admittance, the alternating electrical energization to the element being at a frequency other than the resonance frequency, the admittance of the element at a given frequency of alternating electrical energization being alterable by a mechanical loading of the element;

(b) means for measuring the admittance exhibited by said element, the admittance exhibited by said element being measured in the unloaded condition and when said element is subjected to a mechanical loading on cud element; and (c) means for comparing the measured admittance of said element when said element is in the unloaded condition and the admittance of said element when said element is subjected to mechanical loading to provide an indication of the flow direction of the receiving gas.

58. A method for use with a discharging means discharging a fluid substance into a receiving gas, said method detecting the pressure of the receiving gas, said method comprising the steps of:

(a) placing the discharging means in fluid communication with the receiving gas so that a bidirectional mechanical-electrical conversion element is subjected to a mechanical loading on said element responsive to the gas pressure of the receiving gas;

(b) subjecting the element to mechanical loading responsive to the pressure of the receiving gas; and (c) measuring an electrical output of the element in the loaded condition.

59. The method of claim 58 wherein step (b) is further defined as subjecting a member to pressure exerted by the receiving gas, the member exerting mechanical loading on the element responsive to the gas pressure.

60. The method of claim 59 wherein step (b) is further defined as subjecting a member comprising a porous plate, through which fluid is discharged into the receiving gas by a vibratory action of the element, to the pressure exerted by the receiving gas.

61. The method of claim 59 wherein step (b) is further defined as subjecting a member comprising a piston that discharges fluid into the receiving gas by a vibratory action of the element to the pressure exerted by the receiving gas.

62. The method of claim 58 wherein the bidirectional mechanical-electrical conversion element of the fluid discharging means comprises a piezoelectric element.

63. The method of claim 62 wherein step (b) is further defined as exerting the mechanical loading on the piezoelectric element along an axis of vibration of the piezoelectric element.

64. The method of claim 62 wherein step (b) is further defined as subjecting a member to pressure exerted by the receiving gas, the piezoelectric element is a ring-like piezoelectric element coupled to said member and wherein, in step (b), the pressure of the receiving gases applied to the member causes bowing of the member.

65. The method of claim 59 wherein the bidirectional mechanical-electrical conversion element of the fluid discharging means comprises a bi-morph structure.

66. The method of claim 62 wherein the piezoelectric element is a rod-like element for reciprocating a piston in a fluid filled housing.

67. The method of claim 58 further defined as a method for measuring the pressure of the breathing gases for a subject.

68. The method of claim 58 wherein the fluid discharging means comprises a nebulizer.

69. The method of claim 67 wherein the fluid discharging means comprises a nebulizer.

70. The method of claim 58 further defined as comparing the output of the element to a value for detecting the pressure of the receiving gas.

71. The method of claim 70 further defined as comparing the output of the element to a reference value.

72. The method of claim 70 further defined as comparing an output of the element to a value derived from a previously measured output of the element to determine a difference value and as further comparing the difference value to a reference value to detect the pressure of the receiving gas.

73. Apparatus for discharging a fluid substance into a receiving gas, said apparatus detecting the pressure of the receiving gas, and comprising:

(a) fluid discharging means in fluid communication with the receiving gas, said discharging means having a bidirectional mechanical-electrical conversion element subjected to a mechanical loading responsive to the gas pressure of the receiving gas; and (b) means for measuring an electrical output of said element to detect the pressure of the receiving gas.

74. The apparatus of claim 73 further including a member subjected to the pressure of the receiving gas, said member being coupled to said element for mechanically loading said element.

75. The apparatus of claim 74 wherein said member comprises a plate having perforations through which fluid is discharged into the receiving gas.

76. The apparatus of claim 75 wherein said plate has a ring-like bidirectional mechanical-electrical conversion element coupled thereto and surrounding said perforations.

77. The apparatus of claim 74 wherein said member comprises a piston reciprocating in a fluid filled housing for discharging fluid into the receiving gas.

78. The apparatus of claim 73 wherein said element comprises a piezoelectric element.

79. The apparatus of claim 74 wherein said element comprises a bi-morph structure.

80. The apparatus of claim 73 further defined as one for measuring the pressure of the breathing gases for a subject.

81. The apparatus of claim 73 wherein the fluid discharging means comprises a nebulizer.

82. The apparatus of claim 80 wherein the fluid discharging means comprises a nebulizer.

83. The apparatus of claim 73 further including means for comparing the output of the element to a value to detect the pressure of the receiving gas.

84. The apparatus of claim 83 further including means providing a reference value and wherein said comparing means is further defined as comparing the output of the element to said reference value.

85. The apparatus of claim 83 further including means for deriving a value from a previously measured output of the element, wherein said comparing means determines a difference between said measured value and said derived value, and wherein said apparatus includes means for comparing the difference to a reference value to detect the pressure of the receiving gas.

86. The method of claim 1, 13, or 58 further including the step of operating the discharging means in accordance with the receiving gas pressure indication.

87. The apparatus of claim 36, 39, or 73 further defined as including means for operating said apparatus in accordance with the receiving gas pressure indication.

* * * * *